US012678570B2

(12) United States Patent
Liversidge

(10) Patent No.: US 12,678,570 B2
(45) Date of Patent: Jul. 14, 2026

(54) SAFETY NEEDLE ASSEMBLY FOR USE WITH A MEDICAL INJECTOR

(71) Applicant: TIP-TOP.COM LTD, Colchester (GB)

(72) Inventor: Barry P. Liversidge, Colchester (GB)

(73) Assignee: TIP-TOP.COM LTD, Colchester (GB)

( * ) Notice: Subject to any disclaimer, the term of this patent is extended or adjusted under 35 U.S.C. 154(b) by 372 days.

(21) Appl. No.: 18/283,895

(22) PCT Filed: Mar. 24, 2022

(86) PCT No.: PCT/GB2022/050747
§ 371 (c)(1),
(2) Date: Sep. 25, 2023

(87) PCT Pub. No.: WO2022/200802
PCT Pub. Date: Sep. 29, 2022

(65) Prior Publication Data
US 2024/0165347 A1     May 23, 2024

(30) Foreign Application Priority Data
Mar. 26, 2021    (GB) ..................................... 2104342

(51) Int. Cl.
A61M 5/32         (2006.01)
(52) U.S. Cl.
CPC ... A61M 5/3245 (2013.01); A61M 2005/3224 (2013.01); A61M 2005/3249 (2013.01); A61M 2005/3254 (2013.01)
(58) Field of Classification Search
CPC .............. A61M 2005/3249; A61M 2005/3224
See application file for complete search history.

(56) References Cited

U.S. PATENT DOCUMENTS

| | | | |
|---|---|---|---|
| 4,592,744 A | 6/1986 | Jagger et al. | |
| 9,044,552 B2 * | 6/2015 | Schraga .............. | A61M 5/3257 |

(Continued)

FOREIGN PATENT DOCUMENTS

| | | |
|---|---|---|
| WO | 03015855 A1 | 2/2003 |
| WO | 2004000397 A1 | 12/2003 |

(Continued)

OTHER PUBLICATIONS

International Search Report and Written Opinion from PCT/GB2022/050747; 16 pages; Jul. 15, 2022; Regina Stauber.

(Continued)

*Primary Examiner* — Stephanie Sebasco Cheng
(74) *Attorney, Agent, or Firm* — Dicke, Billig & Czaja, PLLC

(57)         ABSTRACT
A safety needle assembly comprises a blocking member comprising a control member slidably displaceable along a longitudinal axis of a tubular housing from a set position whereat the control member engages a needle mount to maintain a needle in an operative position, thereafter attachment of the safety needle assembly to a medical injector, the use and subsequent detachment of the safety needle assembly from the medical injector, causes the control member to move away from the set position and disengage from the needle mount and allow a spring member to rotate the needle to a shielding position and to move a non-patient end of the needle towards a distal end of the tubular housing whereat the needle extends at an angle oblique to the longitudinal axis of the tubular housing to place the non-patient end of the needle at a location adjacent to an interior wall of the tubular housing.

25 Claims, 13 Drawing Sheets

(56) References Cited

U.S. PATENT DOCUMENTS

| | | | | |
|---|---|---|---|---|
| 2003/0105432 A1* | 6/2003 | Halseth | ............ | A61B 5/150389 |
| | | | | 604/164.12 |
| 2004/0143196 A1 | 7/2004 | Chen | | |
| 2006/0079807 A1* | 4/2006 | Allard | .............. | A61B 5/150656 |
| | | | | 600/576 |
| 2007/0078405 A1* | 4/2007 | Lai | ........................ | A61M 5/322 |
| | | | | 604/110 |
| 2009/0171285 A1* | 7/2009 | Wang | .................... | A61M 5/322 |
| | | | | 604/110 |
| 2010/0317999 A1 | 12/2010 | Shaw et al. | | |
| 2012/0022461 A1* | 1/2012 | Schubert | ............ | A61M 5/3257 |
| | | | | 604/192 |

FOREIGN PATENT DOCUMENTS

| | | | | | |
|---|---|---|---|---|---|
| WO | WO-2009142878 A1 | * | 11/2009 | ........ | A61M 25/0618 |
| WO | 2010079016 A1 | | 7/2010 | | |

OTHER PUBLICATIONS

Written Opinion from PCT/GB2022/050747; 5 pages; Feb. 10, 2023; S. Diamantouros.
International Preliminary Report on Patentability from PCT/GB2022/050747; 20 pages; May 9, 2023; Tanya Saad.

\* cited by examiner

SAFETY NEEDLE ASSEMBLY FOR USE WITH A MEDICAL INJECTOR

FIELD OF THE INVENTION

The present invention relates to a safety device for use with a needle having a sharp tip to confer passive protection to that needle. The present invention also relates to a safety needle assembly for use with a medical injector, a drug delivery device comprising a safety needle assembly and a medical injector and a method of shielding a non-patient end of a needle in a safety needle assembly.

The safety device of the present invention is primarily but not exclusively intended for use with a medical needle. The medical needle may be used to penetrate a human or animal body, or may be used for other medical uses such as the penetration of a pierceable membrane of an intravenous medication system.

In the following description all uses of the needle safety assembly will be described simply as the penetration of a body, even though specific embodiments may be intended for other uses.

BACKGROUND TO THE INVENTION

Fluids of various kinds may be administered to a body by means of a hollow needle in conjunction with a source of the required fluid. For example, such a needle may be associated with a syringe holding a liquid drug, the needle being used to penetrate the body of the site at which a drug is to be administered. Equally, body fluids may be withdrawn by using a hollow needle which is used to penetrate the body until the tip is located at the site from which the fluid is to be withdrawn.

One recognised hazard for clinicians and other persons using or handling needles for the above described purposes, is the risk of a so-called needle stick injury. Such injuries are caused by the accidental penetration by the needle. Prior to the use of the needle to supply a fluid or to withdraw fluid from a body, this rarely presents much of a problem. However, once the needle has been used there is very much a higher risk of serious consequence for the clinician, or others associated with the disposal of a used needle.

Needle stick injuries may be caused by the distal tip of the needle which is used to penetrate through the skin. However, the proximal end of the needle is also sharp since it may be used to pierce or project into a cartridge or container holding the liquid drug. Once the needle mounting assembly is removed from the injecting device, the proximal end of the needle therefore presents a further risk to a clinician or user.

The proximal end of the safety needle assembly may include a shielding device for the distal tip and may also comprise a shroud or skirt which affords some protection of the proximal tip. However, needle stick injuries still result from the proximal end of the needle since the tip is still accessible. In addition, the proximal tip is located centrally within the shroud or skirt such that a fingertip could easily make contact with the proximal end needle tip.

It is an aim of the present invention to overcome at least one problem associated with the prior art, whether referred to herein or otherwise.

SUMMARY OF THE INVENTION

According to a first aspect of the present invention there is provided a safety needle assembly for use with a medical injector comprising;

a tubular housing removably attachable to the medical injector, the tubular housing extending in a longitudinal direction from a proximal end to a distal end, the proximal end being arranged for attachment to the medical injector;

a needle mount located within the tubular housing for directly or indirectly supporting a double ended needle having a patient end and a non-patient end, the needle mount being arranged to allow movement of the needle from an operative position to a shielding position;

a spring means to urge movement of the needle to the shielding position; and a releasable blocking means arranged to prevent movement of the needle from the operative position whereat the needle extends in a direction along a longitudinal axis of the tubular housing and whereby release of the blocking means allows movement of the needle to the shielding position;

characterised in that;

the needle mount is a unitary component inserted into the tubular housing and fixedly retained in a pivoting position so as to rotate around an axis intersecting the longitudinal axis of the tubular housing and the spring means is arranged to urge rotation of the needle about said axis; and the blocking means comprises a control member slidably displaceable along the longitudinal axis of the tubular housing from a set position whereat the control member engages the needle mount to maintain the needle in an operative position before use, thereafter attachment of the safety needle assembly to the medical injector, the use thereof and subsequent detachment of the safety needle assembly from the medical injector, causes the control member to move away from the set position and disengage from the needle mount and allow the spring means to rotate the needle to the shielding position and to move the non-patient end of the needle towards the distal end of the tubular housing whereat the needle extends at an angle oblique to the longitudinal axis of the tubular housing to place the non-patient end of the needle at a location adjacent to an interior wall of the tubular housing.

The longitudinal axis of the tubular housing may be a central longitudinal axis of the tubular housing.

Preferably the spring means is arranged to urge rotation of needle about an axis that intersects and is perpendicular to a central longitudinal axis of the needle.

Preferably the axis of rotation is substantially radial to the longitudinal axis of the housing and/or the central longitudinal axis The control member may be located within the tubular housing or arranged to abut the proximal end of the tubular housing.

Preferably the axis of rotation is statically fixed relative to the tubular housing and the non-patient end moves in a circumferential path about the axis of rotation from the operative position to the shielding position.

The axis of rotation may be radial with respect to the longitudinal axis of the tubular housing. The axis of rotation may be perpendicular with respect to the longitudinal axis of the tubular housing. The axis of rotation may be at an oblique angle with respect to the longitudinal axis of the tubular housing. The axis of rotation may extend across an internal diameter of the tubular housing.

The axis of rotation may intersect the central longitudinal axis of the tubular housing.

The axis of rotation may extend along a chord across the internal area of the tubular housing.

Preferably the needle mount is co-axial with the tubular housing when the needle is in the operative position.

In the shielding position, the non-patient end of the needle may contact or be adjacent to an internal peripheral wall of the tubular housing. In the shielding position, the spring means may urge the non-patient end of the needle against the internal peripheral wall of the tubular housing.

Preferably, in the operative position, the spring mean has stored energy therein.

The spring means may be mounted on (or located adjacent to) an internal wall of the tubular at a first side/portion and wherein the non-patient end of the cannula is arranged to locate adjacent to a second side/portion of the internal wall of the tubular housing. The first side/portion may be an opposite side portion provided on the tubular housing relative to the second side portion. The first side/portion may be 180 degrees offset around the tubular housing relative to the second side/portion. The first side/portion may be longitudinally aligned with the second side/portion.

The spring means may contact the needle mount at a position located distally of the axis of rotation.

The spring means may contact the needle mount at a position located proximally of the axis of rotation.

Preferably the control member comprises an engagement aperture and a part of the needle mount is arranged, in the set position, to locate within the engagement aperture to prevent rotation of the needle from the operative position. The control member may comprise an annular member and the engagement aperture is located centrally on the annular member. The needle mount may comprise a collar which locates within an aperture of the control member in the set positon.

Preferably a distal end of the needle mount provides an outer surface complementary with the engagement aperture of the control member.

The control member may comprise a complementary end face with an end face of a shielding sleeve. Preferably a distal end face of the control member is complementary with a proximal end face of a shielding sleeve.

Preferably the spring means comprises a resilient member which extends inwardly from the tubular housing and contacts an outer surface of the needle mount at a position offset from the axis of rotation and preferably applies a rotational force to rotate the needle mount.

Preferably the spring means comprises a leaf spring projecting inwardly from the tubular housing and, with the needle in an operative position, the leaf spring is in a preloaded condition and may be deflected from a neutral/relaxed position. Preferably with the needle in the operative position the leaf spring has energy stored therein. An end surface of the leaf spring may contact an outer longitudinal surface of the needle mount to create a torque about the axis of rotation.

Preferably the needle mount comprises a unitary component having axial members located on an outer surface. The axial member may provide hemispherical surfaces and may enable the needle mount to be secured by ball and socket arrangements and may enable by a click-fit (ball and socket) arrangement. The tubular housing may comprise axial members located on an internal surface for cooperation with the axial members provided on the needle mount. Preferably the axial members of the needle mount and the tubular housing enable a push fit engagement of the needle mount into the pivoting position within the axial members of the tubular housing. The axial members of the tubular housing and the needle mount may comprise a first pair of axial member comprising projecting portions and a second pair of axial members comprising corresponding recesses. The projecting portions may comprise hemi-spherical projections. The axial members may provide a ball and socket joint. Preferably the axial members provide a first ball and socket joint on one side of the needle mount and a second ball and socket joint on an opposite side of the needle mount for connection to complementary ball and socket joints provided within the tubular housing.

Preferably the control member is mounted to move away from the proximal end (and/or towards the distal end) of the tubular housing in order to disengage the needle mount. The control member may be mounted to move towards the proximal end (and/or away from the distal end) of the tubular housing in order to disengage the needle mount.

Preferably the safety needle assembly comprises a needle shielding sleeve and, in which, the control member may comprise a distal end face of the needle shielding sleeve which provides an or the engagement aperture to prevent rotation of the needle from the operative position whilst the control member is in the set position.

The control member may comprise a disc, the disc being located within a needle shielding sleeve of the safety needle assembly and wherein the disc is slidably displaceable in the needle shielding sleeve from the set position and wherein the control member is frictionally engaged in the needle shielding sleeve and is maintained in a position located adjacent to a distal end of the needle shielding sleeve on movement thereto by the tubular housing during an injection.

The control member may comprise a distal end face and a skirt portion extending therefrom, the distal end face comprising an aperture for engaging an outer surface of the needle mount in the set position and the skirt providing a contact face which is contacted by part of the medical injector and the control member is moved from the set position on attachment of the needle safety assembly to the medical injector.

The control member may be mounted to move towards the proximal end of the tubular housing in order to disengage the needle mount. A needle shielding sleeve may encompass and shield the patient end of the needle in a non-injecting configuration and in which the needle shielding sleeve is co-axial with the tubular housing and may be arranged to slidably move longitudinally relative thereto. A needle shielding sleeve may encompass and shield the patient end of the needle in a non-injecting configuration and, in which, the needle shielding sleeve comprise release means to slidably displace the control member from the set position.

According to a second aspect of the present invention there is provided a drug delivery device comprising a safety needle assembly and a medical injector, the safety needle assembly being in accordance the first aspect of the present invention.

Preferably the medical injector comprises a rubber seal and attachment of the safety needle assembly to the medical injector causes the non-patient end of the needle to pierce and penetrate through the rubber seal and wherein the position of the non-patient end though the rubber seal maintains the needle in an operative position after the control member has moved from the set position.

According to a third aspect of the present invention there is provided a method of shielding a non-patient end of a needle in a safety needle assembly for use with a medical injector, the safety needle assembly comprising;

a tubular housing removably attachable to the medical injector, the tubular housing extending in a longitudinal direction from a proximal end to a distal end, the proximal end being arranged for attachment to the medical injector;

a needle mount located within the tubular housing for directly or indirectly supporting a double ended needle having a patient end and a non-patient end, the needle mount being arranged to allow movement of the needle from an operative position to a shielding position;

a spring means to urge movement of the needle to the shielding position; and a releasable blocking means arranged to prevent movement of the needle from the operative position whereat the needle extends in a direction along a longitudinal axis of the tubular housing and whereby release of the blocking means allows movement of the needle to the shielding position;

characterised in that;

the needle mount is a unitary component inserted into the tubular housing and fixedly retained in a pivoting position so as to rotate around an axis intersecting the longitudinal axis of the tubular housing and the spring means is arranged to urge rotation of the needle about said axis; and the method comprises slidably displacing a control member of the blocking means along the longitudinal axis of the tubular housing from a set position whereat the control member engages the needle mount to maintain the needle in an operative position before use attaching the safety needle assembly to the medical injector, performing an injection with the safety needle assembly and the medical injector, and subsequently detaching the safety needle assembly from the medical injector, which causes the control member to move away from the set position and disengage from the needle mount and allow the spring means to rotate the needle to the shielding position and to move the non-patient end of the needle towards the distal end of the tubular housing whereat the needle extends at an angle oblique to the longitudinal axis of the tubular housing to place the non-patient end of the needle at a location adjacent to an interior wall of the tubular housing.

According to a fourth aspect of the present invention there is provided a safety needle assembly for use with a medical injector comprising;

a tubular housing removably attachable to the medical injector, the tubular housing extending in a longitudinal direction from a proximal end to a distal end, the proximal end being arranged for attachment to the medical injector;

a needle mount located within the tubular housing for directly or indirectly supporting a double ended needle having a patient end and a non-patient end, the needle mount being arranged to allow movement of the needle from an operative position to a shielding position;

a spring means to urge movement of the needle to the shielding position; and a releasable blocking means arranged to prevent movement of the needle from the operative position whereat the needle extends in a direction along a longitudinal axis of the tubular housing and whereby release of the blocking means allows movement of the needle to the shielding position;

characterised in that;

the needle mount is a unitary component inserted into the tubular housing and is fixedly retained in a pivoting position so as to rotate around an axis intersecting the central axis of the tubular housing and the spring means is arranged to urge rotation of the needle about said axis; and the blocking means comprises a control member slidably displaceable along the longitudinal axis of the tubular housing from a set position whereat the control member engages the needle mount to maintain the needle in an operative position before use, wherein movement of the control member away from the set position disengages the blocking means from the needle mount and allows the spring means to rotate the needle to the shielding position which moves the non-patient end of the needle towards the distal end of the tubular housing whereat the needle extends at an angle oblique to the longitudinal axis of the tubular housing to place the non-patient end of the needle at a location adjacent to an interior wall of the tubular housing.

BRIEF DESCRIPTION OF THE DRAWINGS

The present invention will now be described, by way of example only, with reference to the drawings that follow, in which.

DESCRIPTION OF THE PREFERRED EMBODIMENTS

Figure 1:
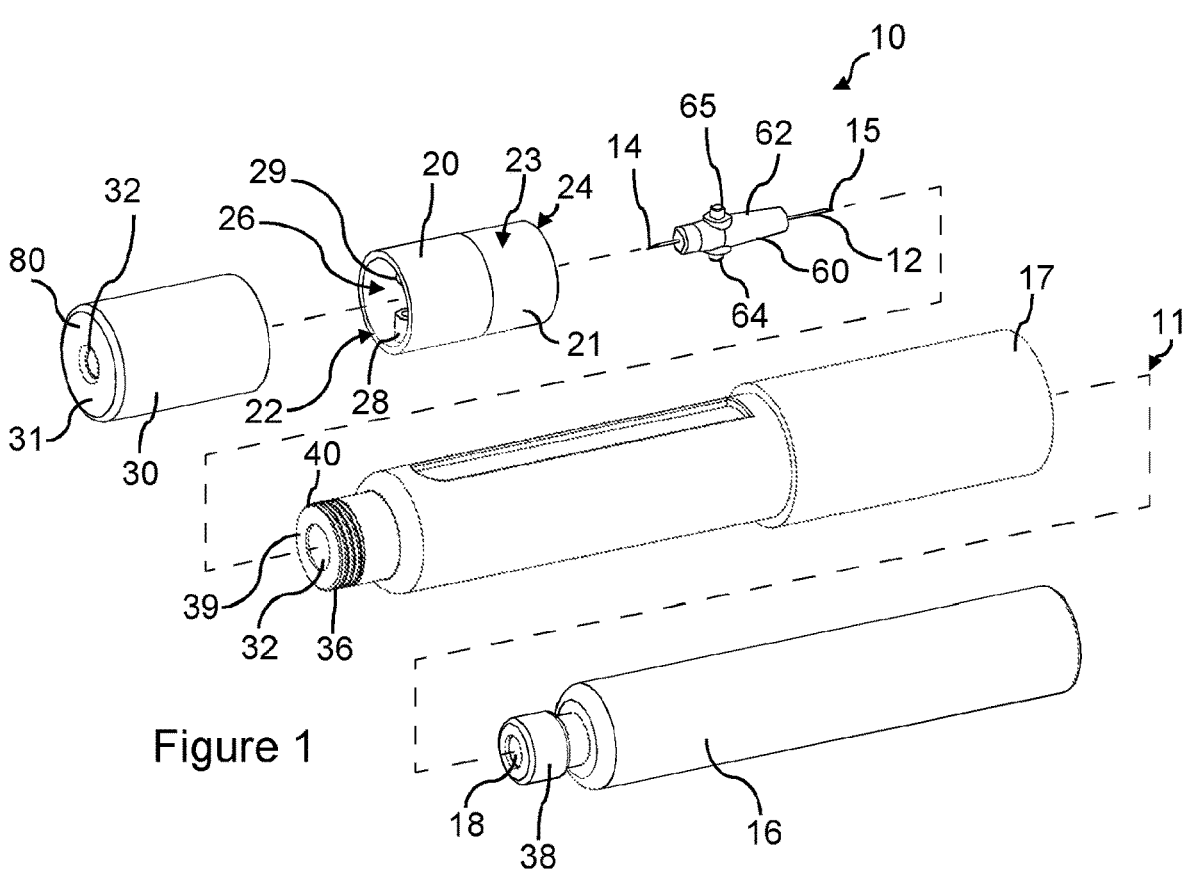
FIG. 1 is an exploded view of a first preferred embodiment of a safety needle assembly together with a medical injector.
Figure 2:
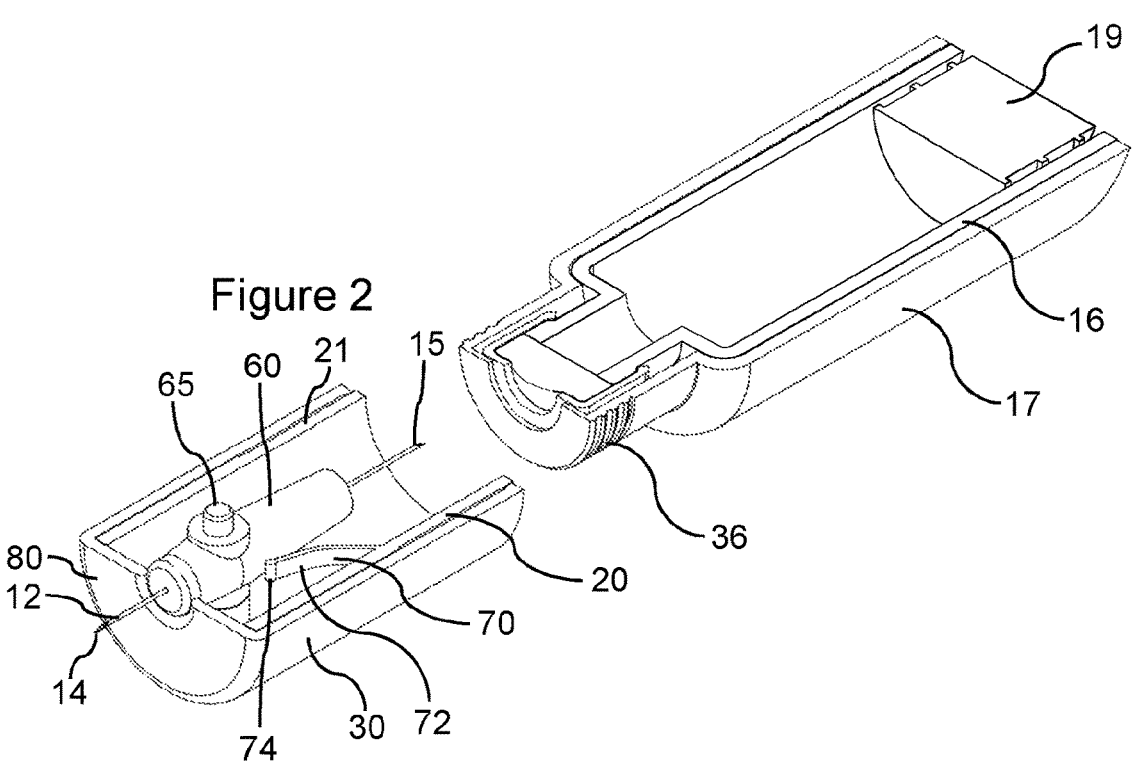
FIG. 2 is a cutaway view of the first preferred embodiment of the safety needle assembly and a medical injector prior to attachment together.
Figure 3:
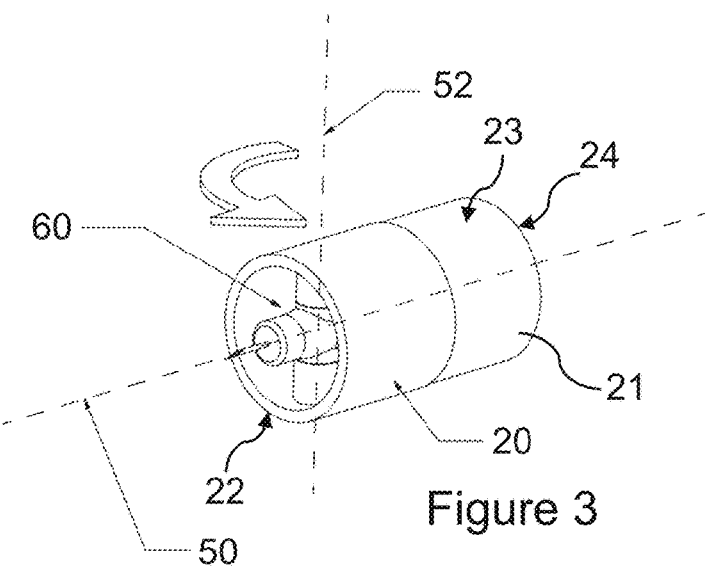
FIG. 3 is a perspective view of a tubular housing, a needle mount and a needle of a first preferred embodiment of the safety needle assembly.

Throughout this specification and with reference to the figures, a safety needle assembly 10 is shown and described herein which provides for shielding of a needle 12 on a pen needle assembly 8 specifically on the non-patient (proximal) end but also, in some embodiments, also on the patient (distal) and. As used herein, the term "distal" and/or "forwards" or "forwardly", and derivatives thereof, refer to the direction generally towards the patient end for use, and the term "proximal" and/or "rearwards" or "rearwardly", and derivatives thereof, is used to describe the direction away from the patient during use.

As shown in the figures and as will be described, the proximal end of the safety needle assembly attached to a distal end of a medical injector 11. The distal end of the safety needle assembly 10 will be pressed against the skin of patient during an injection and the distal end of the medical injector 11 locates away for the patient.

Throughout the following description of the preferred embodiments of safety device of this invention, the same reference characters are used to identify corresponding parts of the various embodiments.

The present invention may be used with pen injectors and will be described by way of example as being used with a pen injector. Drug delivery devices 8 generally include a medical injector 11 including a dose-adjustment mechanism for setting a dose, for example of insulin, and a pen needle 12 provided on a safety needle assembly 10 for insertion into a patient to allow proper drug administration. The pen comprises a single use needle 12 and is removed and disposed of after each administered dose.

The pen needle 12 is a double ended needle 12 and includes a patient end 14 or distal end comprising a sharp tip for insertion into a patient. The double ended needle 12 also includes a non-patient end 15 or proximal end comprising a sharp tip for insertion into a drug vial or cartridge 16 provided by the pen injector 11. The proximal/non-patient end 15 of the needle will typically have to pierce a rubber seal 18 which may comprise a septum or stopper provided on the end of the vial or cartridge 16 to access the liquid medicament or drug contained within the cartridge. Devices have been developed in the prior art to shield the distal, or patient end of the needle 12 to prevent an inadvertent "needle stick" after use. Even with the distal end 14 being shielded, the proximal, or non-patient end 15 of the needle 12 is exposed after the detachment of the safety needle assembly 10 from the medical injector 11.

Figure 4:
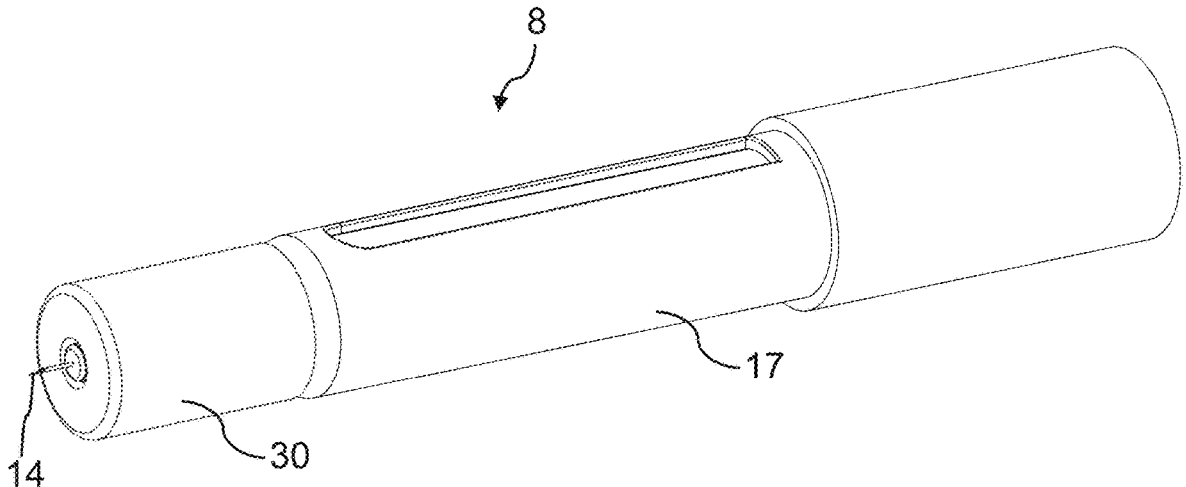
FIG. 4 is a perspective view of a pen injector comprising the first preferred embodiment of the safety needle assembly attached to a medical injector.

With reference to FIG. 1, a safety pen needle assembly 10 and a medical injector 11 are shown in an exploded view and FIG. 4 shows the complete drug delivery device 8 in an assembled configuration. The safety needle assembly 10 generally includes a hub or tubular housing 20, a needle 12, a shielding sleeve 30. The tubular housing 20 includes a body 21 extending in a longitudinal direction from a proximal end 24 to a distal end 22. The proximal end 24 is formed with an open face open and is shaped to receive a portion of the injector 11 to allow the attachment of the safety needle assembly 10 to the injector 11. As will be described below, corresponding attachment features are provided on the tubular housing 20 adjacent to the proximal end 24 formed to cooperate with mounting features provided on a distal end of the injector 11. For example, the mounting features may be threads or a surface configuration, such as a tapered surface for a push-fit mounting, or both. The needle 12 may be of any needle design, particularly of any pen needle design. For the description of the present invention, the term cannula 12 will now be used to specifically refer to the double ended needle of the safety needle assembly 10. The cannula 12 includes a distal end 14 formed for insertion into a patient, and a proximal end 15. As shown in the figures, the distal end 14 of the cannula 12 protrudes distally beyond the distal end 22 of the tubular housing 20. The proximal end 15 of the cannula 12 may be within the interior of the tubular housing 20 adjacent to the proximal end 24, or may protrude/extend proximally from the proximal end 24 (this arrangement is not shown). The cannula 12 is mounted within a needle mount 60 and may be fixed therein using any known technique, such as being adherently fixed to the needle mount 60.

Specific embodiments of the present invention will now be described. As shown in FIG. 1, a drug delivery device 8 in the form of a medical pen or injector pen comprises a safety needle assembly 10 which is arranged, in use, to be attached to the medical injector 11. The medical injector 11 comprises a cartridge 16 containing a medicament/fluid and, in particular, the cartridge 16 contains a volume of liquid medicament.

The cartridge 16 is secured within a housing 17. A plunger assembly (not shown) includes a piston 19 or stopper which is used to force the liquid medicament from the cartridge 16. The cartridge 16 comprises a crimped cap 38 and a rubber seal 18. The rubber seal 18 forms a seal to contain the liquid medicament and is pierceable by a proximal end 15 of a cannula 12 (double ended needle) as will be described in more detail below.

The cartridge 16 locates within the housing 17 and the crimped cap 38 locates within a distal end of the housing 17. The distal end of the housing 17 includes a boss 40 including an aperture 32 provided on a distal end face 39 which, when assembled, aligns with the rubber seal 18 and provides an access window to the rubber seal 18 such that the rubber seal 18 is exposed and accessible through the window.

The present invention provides a safety needle assembly 10 which is attachable to the medical injector 11. The safety needle assembly 10 provides the cannula 12 through which the liquid medicament is delivered from the cartridge 16 to the patient. The cannula 12 comprises a double ended needle having a sharp tip at the patient end (distal end) 14 and also a sharp tip at the non-patient end (proximal end) 15. However, it should be appreciated that the terms needle and cannula are used interchangeably and the present invention may also be suitable for other types of drug delivery devices 8. The present invention is suitable for use with needles or cannulas 12 and aims to prevent needle stick injuries caused by the proximal/non-patient end 15 of the needle or cannula 12.

In order to deliver the liquid medicament, the cannula 12 is held in an operative position. In this operative position, the linear cannula 12 protrudes directly out of the end of the drug delivery device 8 and, specifically, the cannula 12 extends along the (central) longitudinal axis 50 of the tubular housing 20. Accordingly, in this operative position, the cannula 12 is located in a central co-axial position within the tubular housing 20. This co-axial position enables the cannula 12 to protrude perpendicularly from a front face 31 of the needle safety assembly 10.

The safety assembly 10 provides a front face 31 having a central window or aperture 32 through which the cannula 12 projects or is projectable. In the first preferred embodiment, the safety needle assembly 10 is provided with an end cap in the form of a shielding sleeve 30 which includes the central window 32. In the first preferred embodiment, the shielding sleeve 30 or end cap functions as a blocking means in the form of a control member 80 to retain the position of the cannula 12 and to release the cannula 12 as will be described below.

The control member 80 or shielding sleeve 30 is mounted to the tubular housing 20. The control member 80 or shielding sleeve 30 locates over the outer surface 23 of the tubular housing 20 and is retained thereto. However, control member 80 or shielding sleeve 30 is slidably movable in a longitudinal direction relative to the tubular housing 20. The significance of this longitudinal sliding movement will be described later.

The housing 17 of the injector 11 has a distal end providing an external screw thread 36 to engage with an internal screw thread 37 provided on the safety needle assembly 10. Specifically, the proximal end 24 of the tubular housing 20 provides the internal screw thread 37 for attaching the safety needle assembly 10 to the housing 17.

The cannula 12 is secured within a needle mount 60. The needle mount 60 is arranged to be fixed within the tubular housing 20 in order to secure the cannula 12 within the safety needle assembly 10. The needle mount 60 is provided with two axial members in the form of lugs 64, 65 for engagement within two corresponding axial members in the form of recesses 28, 29 provided internally on the tubular housing 20. In particular, the tubular housing 20 defines a rotational axis which may be a fixed rotational axis about which the cannula 12 is able to rotate (or pivot). Such movement is functionally important to the present invention and enables the cannula 12 to rotate from an operative position to a shielding positon. In the shielding positon, the non-patient end 15 of the cannula 12 is shielded to prevent and/or inhibit back end needle stick injuries. As will be described, a fixed rotational axis may be provided by axle elements which are engaged within corresponding recesses to prevent any other relative movement apart from the rotational/pivoting action of the needle mount 60 relative to the tubular housing 20. In alternative embodiments, the rotational/pivoting functionality may be provided by a flexible section such as a live hinge arrangement whereby the rotational axis may not be statically fixed to solely provide rotation about a static rotational axis. The present invention will be described with reference to static rotational axes.

As will be described, the cannula 12 is arranged to rotate (or pivot) about a fixed axis 52 (or fixed point) in the tubular housing 20. In the operative position, the cannula 12 extends along the central longitudinal axis of the tubular housing 20. The fixed axis 52 for rotation extends perpendicularly and intersects the central longitudinal axis 50. The fixed axis 52 extends diametrically across the tubular housing 20 and extends radially from the central longitudinal axis 50. This creates a fixed axis 52 or fixed pivoting point or fixed point of rotation for the cannula 12 which is located on the central longitudinal axis 50.

As mentioned above, the cannula 12 is arranged to rotate about the fixed axis 52 from an operative position in which the cannula 12 extends along the central longitudinal axis 50 to a shielding position in which the cannula 12 extends at an angle to the central longitudinal axis 50. In particular, in the shielding position, the cannula 12 extends in a direction oblique to the central longitudinal axis 50.

Due to the fixed axis 52 and fixed point of rotation for the cannula 12, the movement from the central longitudinal axis 50 to an oblique position causes the non-patient end 15 of the cannula 12 to move towards the internal wall 26 of the tubular member 20. In this position with the non-patient end 15 of the cannula 12 towards and adjacent to the internal wall 26 of the tubular housing 20, the non-patient end 15 is shielded to a greater degree and provides significantly reduced risk of creating a needle stick injury. Furthermore, as a result of the fixed axis 52, the pivoting action of the needle about the fixed point located on the central longitudinal axis 50 means that the non-patient end 15 of the cannula 12 also moves forwardly (in a distal direction) and away from the open end 24 of the tubular housing 20. This movement of the non-patient end 15 of the cannula 12 in a distal direction of the longitudinal axis 50 of the tubular housing 20 thereby increases the distance between the open end 24 of the tubular housing 20 and the non-patient end 15 of the cannula 12. This increases the level of protection afforded by increasing the distance by which a tip of a finger would need to be inserted into the open end 24 of the tubular housing 20 in order to make contact with the non-patient end 15 of the cannula 12. This increased separation distance coupled with the non-patient end 15 also being located adjacent to the wall 26 of the tubular housing 20 provides increased safety for users from needle stick injuries.

The increased safety arises from the arcuate or circumferential travel/movement of the non-patient end 15 of the cannula 12 as will be further described below. The present invention provides a passive safety system which causes the cannula 12 to move from the operative position to the shielding position automatically without any specific intervention or action by the user. In particular, as is the case with normal pen injector systems, detachment of the safety needle assembly 10 from the injector 11 exposes the open end 24 of the tubular housing 20 and potentially the non-patient end 15 of the cannula 12 and thereby creates the opportunity for needle stick injuries at the back end. Accordingly, as will be described below, the present invention provides a system through which the cannula 12 moves to the improved shielding position automatically on detachment of the safety needle assembly 10 from the injector 11. A blocking system is arranged to retain the cannula 12 in the operative position before attachment of the safety needle assembly 10 to the medical injector 11. Furthermore, the blocking system maintains the cannula 12 in the operative position prior to use and before attachment of the safety needle assembly 10 to the injector 11. In particular, before use, the blocking system retains the non-patient end 15 in a piercing position such that the non-patient end 15 is located centrally relative to the periphery of the open end 24 of the tubular housing 20. As the injector 11 is attached to the safety needle assembly 10, the non-patient end 15 of the cannula 12 pierces the rubber seal 18 of the cartridge 16 in order to penetrate into the internal reservoir comprising the liquid medicament. Accordingly, the non-patient end 15 is located co-axially central within the tubular housing 20 in order for the tip 15 to pierce and to locate within cartridge 16.

The use and operation of the first preferred embodiment of the present invention will now be described with reference to FIG. 1 to FIG. 7. As described above, the drug delivery device 8 comprises the safety needle assembly 10 and the pen injector 11 and these are shown detached, prior to use, in FIG. 2. In this position, the cannula 12 is held in an operative position and, specifically, the non-patient end 15 of the cannula 12 is positioned along the central longitudinal axis 50 of the tubular housing 20.

The cannula 12 is secured within the needle mount 60 which provides two axle lugs 64, 65 on opposing sides. The axle lugs 64, 65 are received within two corresponding recesses 28, 29 in the tubular housing 20 such that the cannula 12 is rotatable about a fixed axis 52 within the tubular housing 20.

The safety needle assembly 10 is attached to the pen injector 11 using the screw threads 36, 37 provided on the end of the pen injector 11 and also on the tubular housing 20. As the safety needle assembly 10 is brought into engagement with the pen injector 11 the non-patient end 15 of the cannula 12 abuts, pierces and then projects through the rubber seal 18. During this attachment, the cannula 12 is held along the central longitudinal axis 50 in order to assist with the smooth movement of the cannula 12 through the rubber seal 18.

Figures 5A, 5B, 6:
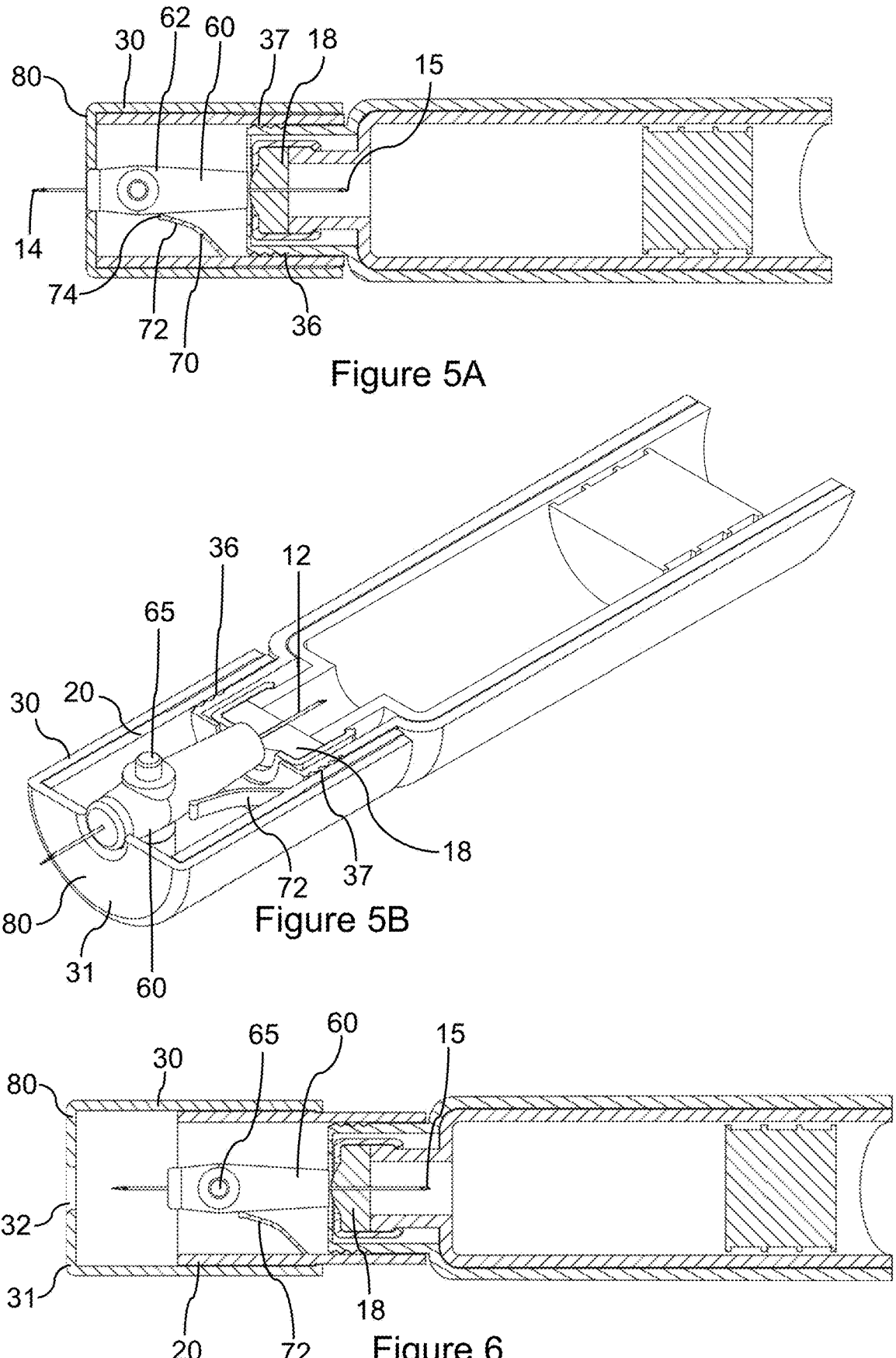
FIG. 5A is cross section of the first preferred embodiment of the safety needle assembly attached to a medical injector ready to perform an injection.
FIG. 5B is a cutaway view of the first preferred embodiment of the safety needle assembly and a medical injector attached together ready to perform an injection.
FIG. 6 is of a cross-section of the first preferred embodiment of the first preferred embodiment of the safety needle assembly attached to a medical injector after an injection.

Once attached, the non-patient end 15 of the cannula 12 locates within the central reservoir of the cartridge as shown in FIG. 5A and FIG. 5B.

The tubular housing 20 includes spring means in the form of a leaf spring 70 in the form of a resilient finger 72 which projects inwardly from the internal surface 26 of the tubular housing 20. The resilient finger 72 includes a contact tip 74 which contacts or abuts an outer surface of the needle mount body 62 at a position located offset from the fixed axis 52 of rotation defined by the axial members 28, 29, 64, 65. Accordingly, in the operative position, the resilient finger 72 is in a configuration whereby the tip 74 exerts a force, specifically a moment or torque, on the outer surface of the needle mount 60. Accordingly, in the operative position, the resilient finger 72 is not in a neutral position and is in a deflected state relative to the neutral relaxed condition/state/position. In particular, in the operative position, the leaf spring 70/resilient finger 72 is preloaded such that energy is stored within the leaf spring 70/resilient finger 72. This stored energy acts to urge the cannula 12 away from the operative position and away from being aligned with the longitudinal axis of the tubular housing 20. Before assembly of the needle mount 60 within the tubular housing 20, the leaf spring 70/resilient finger 72 is in a neutral state with no stored energy. On mounting of the needle mount 60 within the tubular housing 20, the leaf spring 70/resilient finger 72 is deflected and moved to store energy which acts to urge the needle mount 60 away from the operative position. On release of the cannula 12/needle mount 60 by both the control member 80 and the rubber seal 18, the non-patient end 15 of the cannula 12 locates adjacent to the internal wall 26 of the tubular housing 20. In this configuration, the leaf spring 70/resilient finger 72 would typically not be the neutral position and energy is still stored such that the leaf spring 70/resilient finger 72 continues to press and urge the non-patient end 15 of the cannula 12 against the internal wall 26 of the tubular housing 20.

The needle mount 60 is maintained in the operative position by control means which engages a part of the needle mount 60 and maintains the cannula 12 in the operative positon. In the first preferred embodiment, the blocking means is provided by the shielding sleeve 30 which includes the central aperture 32. The central aperture 32 engages around a front end of the needle mount 60. In addition, the shielding sleeve 30 is secured around the tubular housing 20 and is only able to move longitudinally with respect to the tubular housing 20 in a distal direction. Accordingly, in the set position shown in FIGS. 5A and 5B, the front end of the needle mount 60 is secured within the aperture 32 of the shielding sleeve 30 such that any force exerted by the resilient finger 72 is counteracted and does not cause rotation of the needle mount 60 or cannula 12 about the fixed axis 52.

In this set position, it can be seen that the patient end 14 of the needle protrudes/projects outwardly from the drug delivery device 8 and is thereby able to inject a patient and to deliver the liquid medicament from the pen injector 11. Once the injection has been completed, the shielding sleeve 30 is moved forwardly to a shielding position. The specific details of the arrangement of the front shielding sleeve 30 are not provided in this specification and there are many suitable devices available, for example as described in WO2011/092518. In particular, the shielding sleeve 30 slides in a distal direction longitudinally relative to the tubular housing 20, as shown in FIG. 6. In this position, the needle mount 60 is no longer engaged within the aperture 32 of the shielding sleeve 30 and can no longer prevent the spring means rotating the needle mount 60 about the fixed axis 52. However, the non-patient end 15 of the cannula 12 remains engaged within the rubber seal 18 along the longitudinal axis 50 such that this arrangement still prevents rotation of the needle mount 6040 about the fixed axis 52.

Figure 7A:
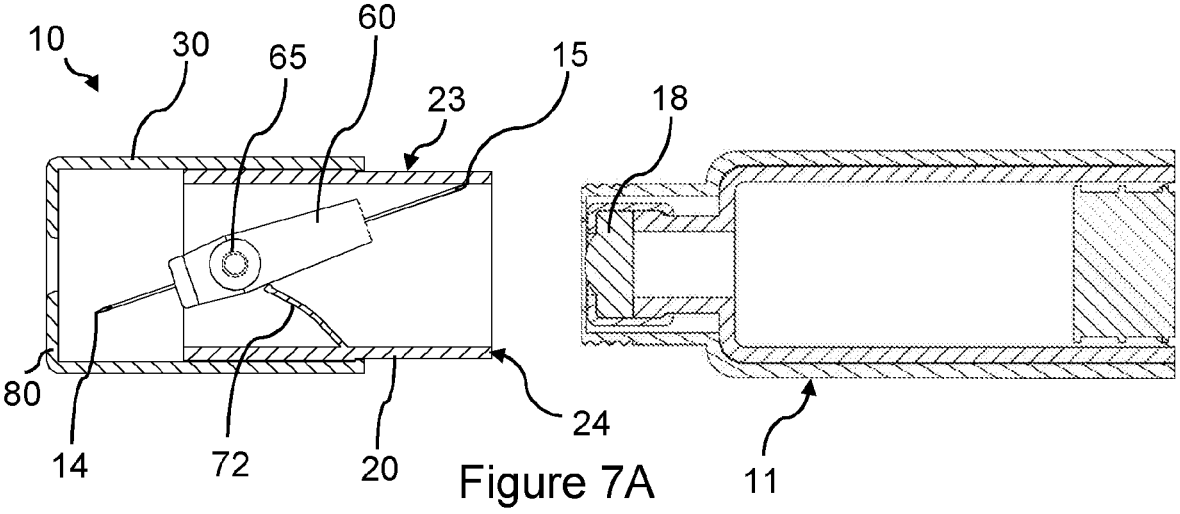
FIG. 7A is a cross-section of the first preferred embodiment of the safety needle assembly detached from a medical injector in a used configuration.
Figure 7B:
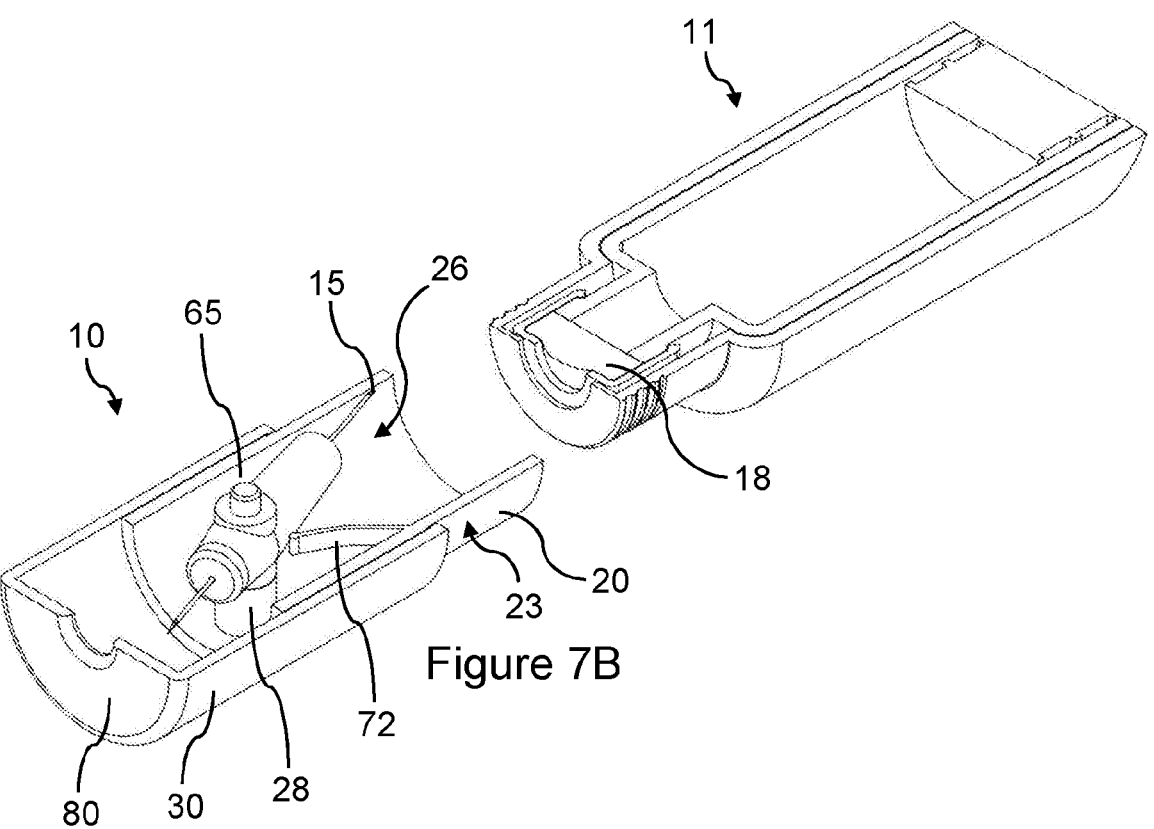
FIG. 7B is a cutaway view of the first preferred embodiment of the safety needle assembly detached from a medical injector in a used configuration.

After use the safety needle assembly 10 requires disposal and is, therefore, detached from the medical injector 11 through use of the threaded surfaces 36, 37 to detach and unscrew the safety needle assembly 10. As shown in FIG. 7A, on detachment, the non-patient end 15 of the cannula 12 is withdrawn back through and disengaged from the rubber seal 18 and is therefore no longer held by the rubber seal 18 along the longitudinal axis 50 of the tubular member 20. In this configuration, there is no restraining means preventing rotation of the needle mount 60 due to the exerted torque of the resilient finger 72 and, therefore, the needle mount 60 automatically rotates about the fixed axis 52, as shown in FIGS. 7A and 7B.

Due to the length of the cannula 12 and/or the energy stored in the resilient finger 72, the needle mount 60 rotates about the fixed axis 52 until the non-patient end 15 of the cannula 12 locates adjacent to and, preferably, abuts the internal side wall 26 of the tubular housing 20. As a result of the fixed axis 52 of the needle mount 60, the non-patient end 15 of the cannula 12 moves in a distal direction and circumferentially about the axis 52 in an arcuate direction such that the distance along the longitudinal extent between the non-patient end 15 and the open face 24 of the tubular housing 20 increases. Accordingly, not only does the non-patient end 15 locate adjacent to the internal wall 26 of the tubular housing 20 but the non-patient end 15 is also withdrawn/retracted into the tubular housing 20 which significantly increases the protection afforded from needle stick injuries. Both the sideways, radial movement of the non-patient end 15 and the retraction/withdrawal movement in the distal direction of the non-patient end 15 are performed automatically and simultaneously such that the present invention provides improved passive needle stick protection. Furthermore, in the shielding position, the leaf spring 70 may continue to exert a pivoting/rotating force on the needle mount 60 and this presses the non-patient end 15 of the cannula 12 against the internal wall 26 of the tubular housing 20.

Furthermore, it will be noted that the patent end 14 of the cannula 12 locates in a position which is not aligned with the aperture 32 of the shielding sleeve 30 such that the longitudinal sliding movement of the shielding sleeve 30 would not cause the patient end 14 of the cannula 12 to project through the aperture 32 in order to present a further risk.

Overall, in the first embodiment, the safety needle assembly 10 does not have a separate control member 80 since this functionality is provided by the needle shielding sleeve 30. Briefly, the spring 70 is arranged to urge rotation of the needle mount 60 about an axis generally perpendicular to and intersecting a longitudinal axis 50 of the cannula 12. However, the control member 80 (shown located at a first position relative to the needle mount in FIG. 5A and FIG. 5B) prevents rotation of the needle mount 60. As the safety needle assembly 10 (pen needle) is screwed onto the injector 11 (pen injector), the non-patient end 15 of the needle 12 pierces the rubber seal 18 of the cartridge 16 and enters into the drug reservoir within the pen injector 11. The needle shielding sleeve 30 is already retracted and in the injecting configuration and the drug can now be delivered into the patient. The pen needle 10 is removed from the injection site and the needle shielding sleeve 30 can now be moved forward and locked safely in a needle shielding position automatically. As mentioned above, the mechanism for moving the shielding sleeve is not described herein and a suitable arrangement is provided in WO2011/092518. However, the needle mount 60 cannot rotate (even though the control member 80 is no longer preventing rotation of the needle mount 60) because the non-patient end 15 of the cannula 12 is still inserted into the rubber seal 18 of the pen injector reservoir. When the pen needle 10 is disconnected (detached) from the pen injector 11 the spring 70 can then rotate the needle mount 60 to "safely park" the non-patient end 15 of the cannula 12 so that the pointed end of the cannula 12 abuts against the inside wall 26 of the tubular housing 20.

The operation and use of further preferred embodiments will now be described in relation to FIGS. 8-28.

A second preferred embodiment, as shown in FIG. 8 to FIG. 12, includes a blocking means comprising a control member 180 in the form of an annular component 182 in the form of a disc which is separate from the shielding sleeve 130. In the configuration before use, with the safety needle assembly 110 not having been attached to the pen injector 111, the needle mount 160 is again held in the operative position by the control member 180. As mentioned above, in this embodiment, the control member 180 comprises an annular component 182 or disc with a central aperture 184 which aligns with, and engages, an outer surface 161 of the front portion of the needle mount 160 in a similar way as described above. However, the shielding sleeve 130 of this second preferred embodiment, acts as a shield which protects the patient end 114 of the cannula 112 prior to use. The operation of this embodiment is the same as described above in that the tubular housing 120 is attached to the injector 111 through the use of the screw threads and this causes the non-patient end 115 of the cannula 112 to pierce and penetrate through the rubber seal 118 into the internal volume of the cartridge 116.

Figures 8, 9:
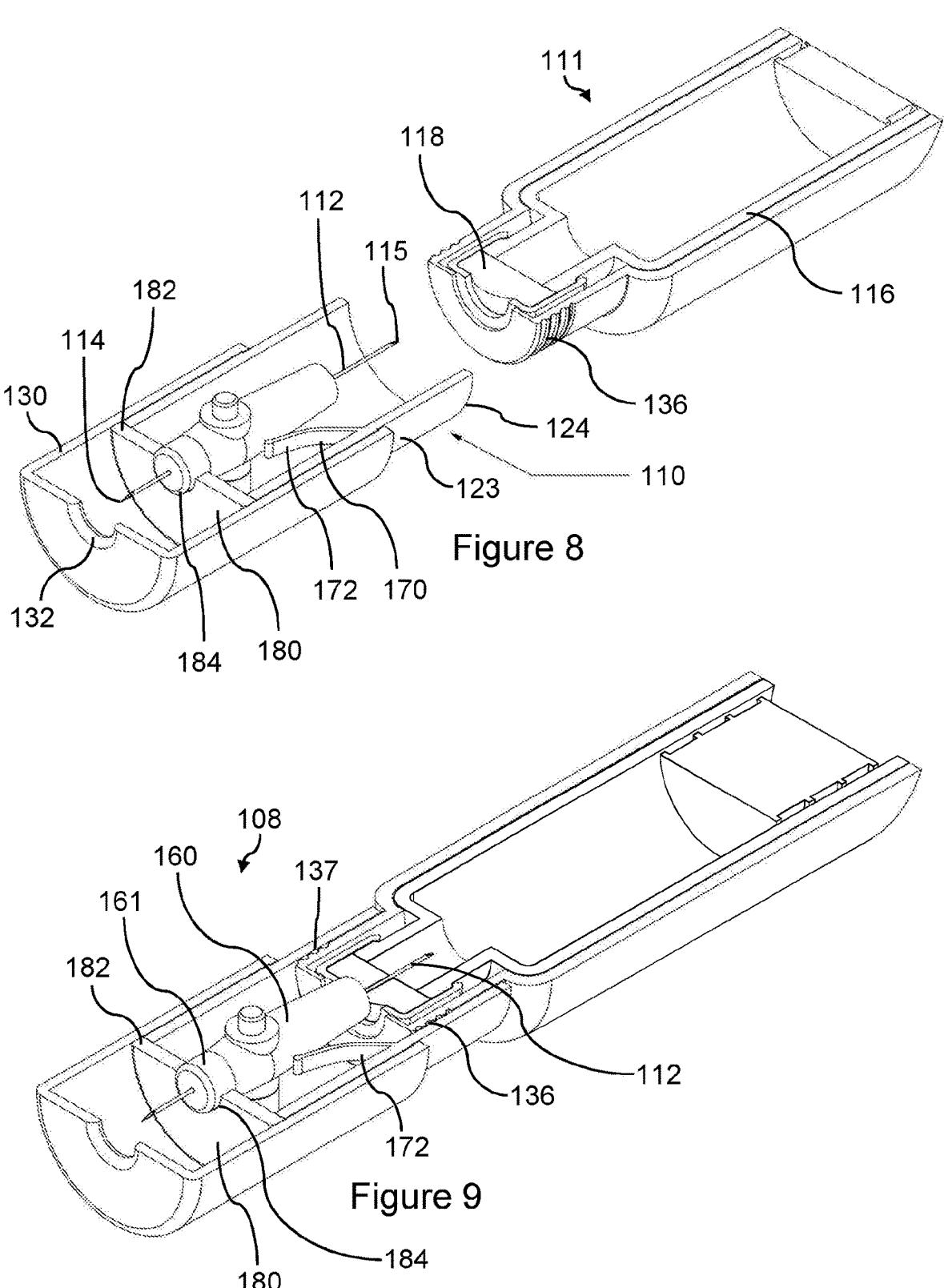
FIG. 8 is a cutaway view of a second preferred embodiment of a safety needle assembly prior to attachment to a medical injector.
FIG. 9 is a cutaway view of the second preferred embodiment of the safety needle assembly attached to a medical injector and ready to perform an injection.
Figures 10, 11, 12:
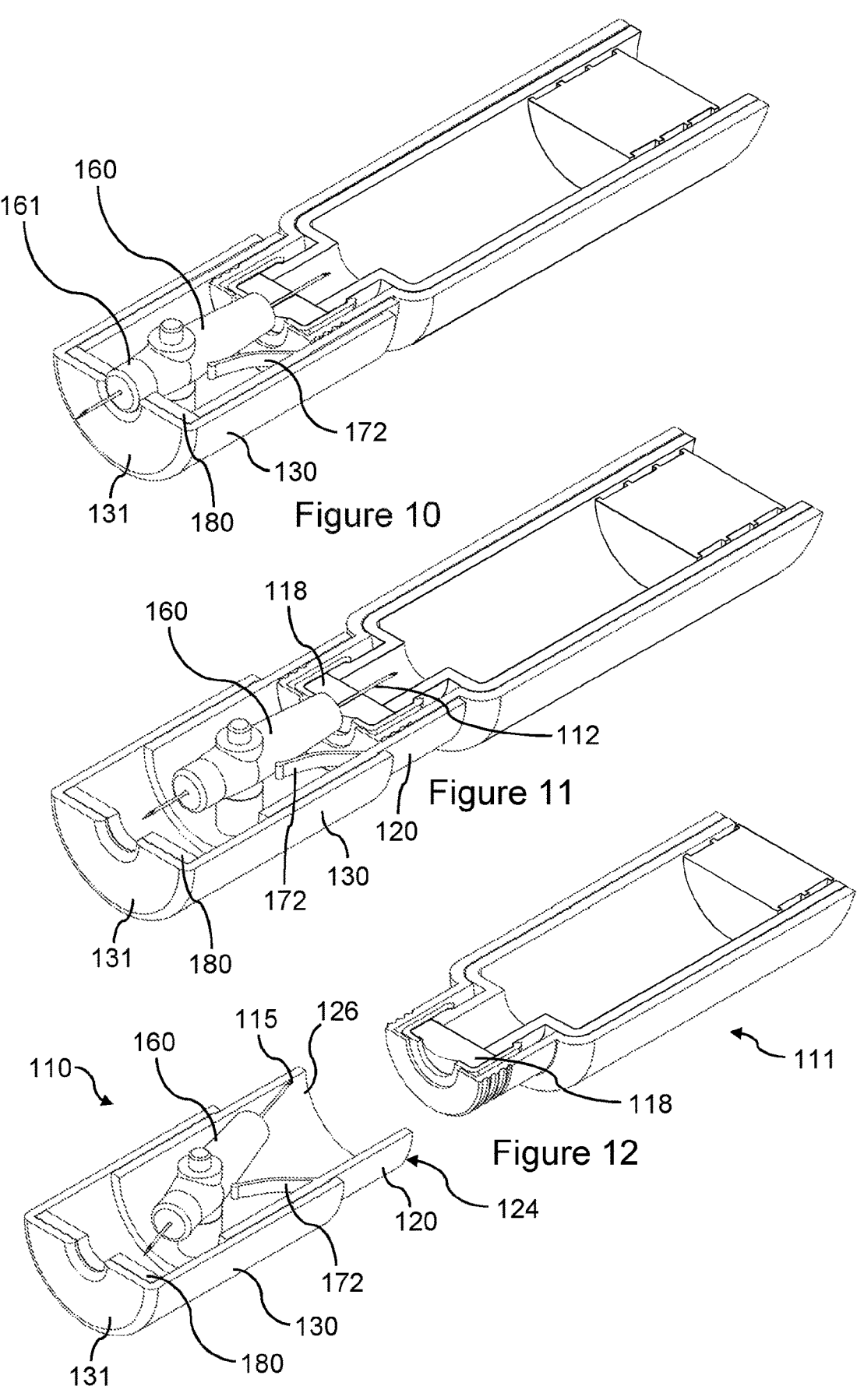
FIG. 10 is a cutaway view of the second preferred embodiment of the safety needle assembly and a medical injector performing an injection.
FIG. 11 is a cutaway view of the second preferred embodiment of the safety needle assembly and a medical injector after an injection.
FIG. 12 is a cutaway view of the second preferred embodiment of the safety needle assembly after use and disconnected (detached) from a medical injector.
Figure 13:
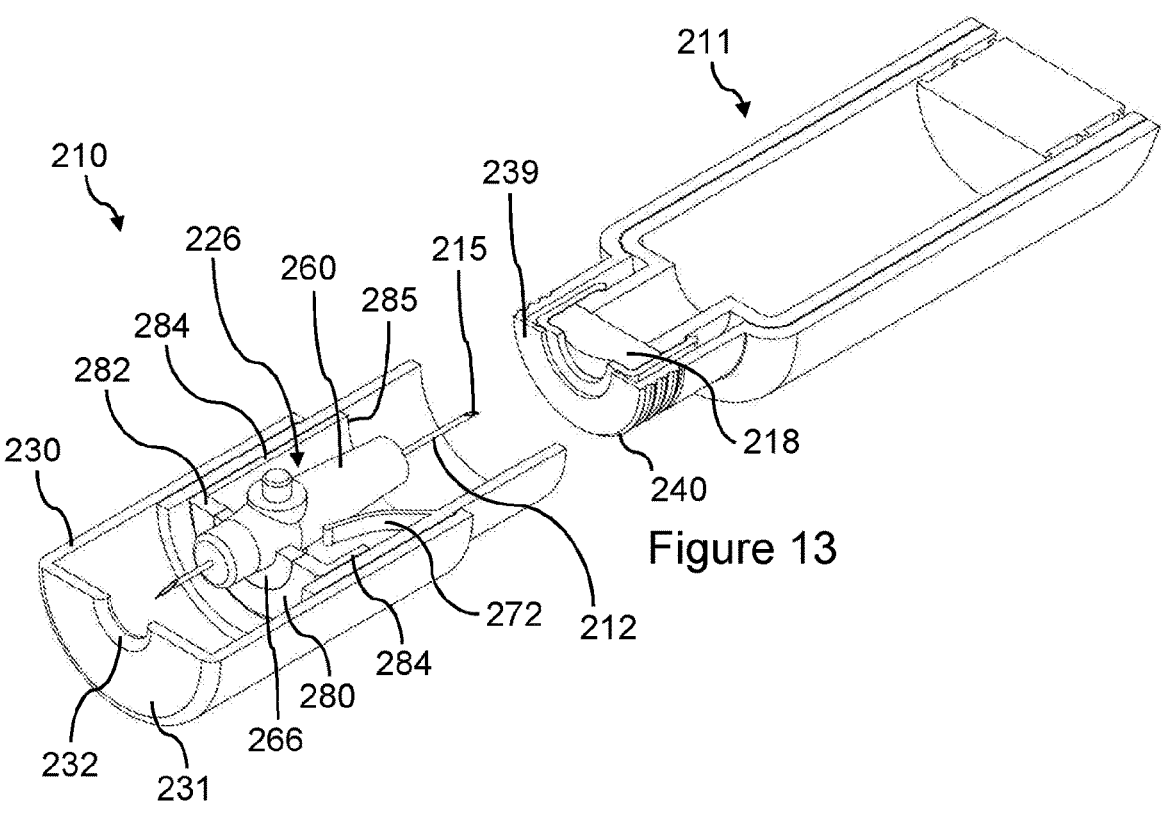
FIG. 13 is a cutaway view of a third preferred embodiment of a safety needle assembly prior to attachment to a medical injector.

FIG. 9 shows the drug delivery device 108 in the set position with the drug delivery device 108 ready for use. The shielding sleeve 130 is slidably movable over the tubular housing 120 in the longitudinal direction. In particular, the shielding sleeve 130 may comprise spring means (not shown) to urge the shielding sleeve 130 to move in a distal direction to the outer position shown in FIG. 9. In order to perform an injection, the front face 131 of the shielding sleeve 130 is pressed against the skin of the patient and the shielding sleeve 130 slidably moves over the tubular housing 120 towards the injector 111. The patient end 114 of the cannula 112 projects through the central aperture 132 provided in the shielding sleeve and into the patient in an injecting configuration On full retraction of the shielding sleeve 130 over the tubular housing 120, the cannula 112 may protrude by a pre-set amount in order to perform the required injection. In this position, the control member 180 (annular component 182) locates adjacent to the front (distal) end of the shielding sleeve 130, as shown in FIG. 10.

Once the liquid medicament has been delivered, the drug delivery device 108 is moved away from the skin of the patient and spring means (not shown) may push the shielding sleeve 130 in a distal direction relatively away from the injector 111 and slidably moves the shielding sleeve 130 over the tubular housing 120 to the used position (not shown) and a locking means locks the shield in the used position (not shown). The control member 180 in the form of the annular component 182 is retained in the outer/distal position adjacent to the distal end of the shielding sleeve 130 through frictional engagement or other latching arrangement. This thereby automatically or passively releases the control member 180 on performing an injection from engagement with the needle mount 160 since the tubular housing 120 comprising with needle mount 160 moves with the injector 111 away from the skin of the patient. Accordingly, in this configuration, the control member 180 no longer retains the cannula 112 in the operative positon. However, the cannula 112 is maintained in the operative position through the engagement of the non-patient end 115 of the cannula 112 with the rubber seal 118. It should be noted that the control member 180 in this embodiment may also provide a visual indication that the injection has been performed correctly and to the correct depth since it is retained at a visible position at the distal end.

As before, the safety needle assembly 110 is now able to be detached from the pen injector 111 through the release of the screw threads 136, 137. Once the non-patient end 115 of the cannula 112 is moved through the rubber seal 118 and is released thereby, the leaf spring 170 in the form of the resilient finger 172 then rotates the needle mount 160 to the shielding position, as shown in FIG. 12. Again, this movement is automatic and provides passive needle stick protection.

In the shielding positon, the non-patient end 115 of the cannula 112 locates adjacent to the internal wall 126 of the tubular housing 120. Furthermore, due to the location of the fixed axis of the movement, the non-patient end 115 of the cannula 112 is withdrawn further into the tubular housing away from the open end 124 to provide significantly greater protection. The axis 52 for movement of the cannula 112 intersects a longitudinal axis of the tubular housing 120 and the point of contact of the leaf spring 170 on the needle mount 160 is arranged to ensure that the non-patient end 115 moves distally and not proximally. Prior to detachment of the safety needle assembly 110 from the medical injector 111, the non-patient end 115 penetrates the rubber seal 118 and this holds the cannula along the longitudinal axis of the tubular housing 120.

Figure 14:
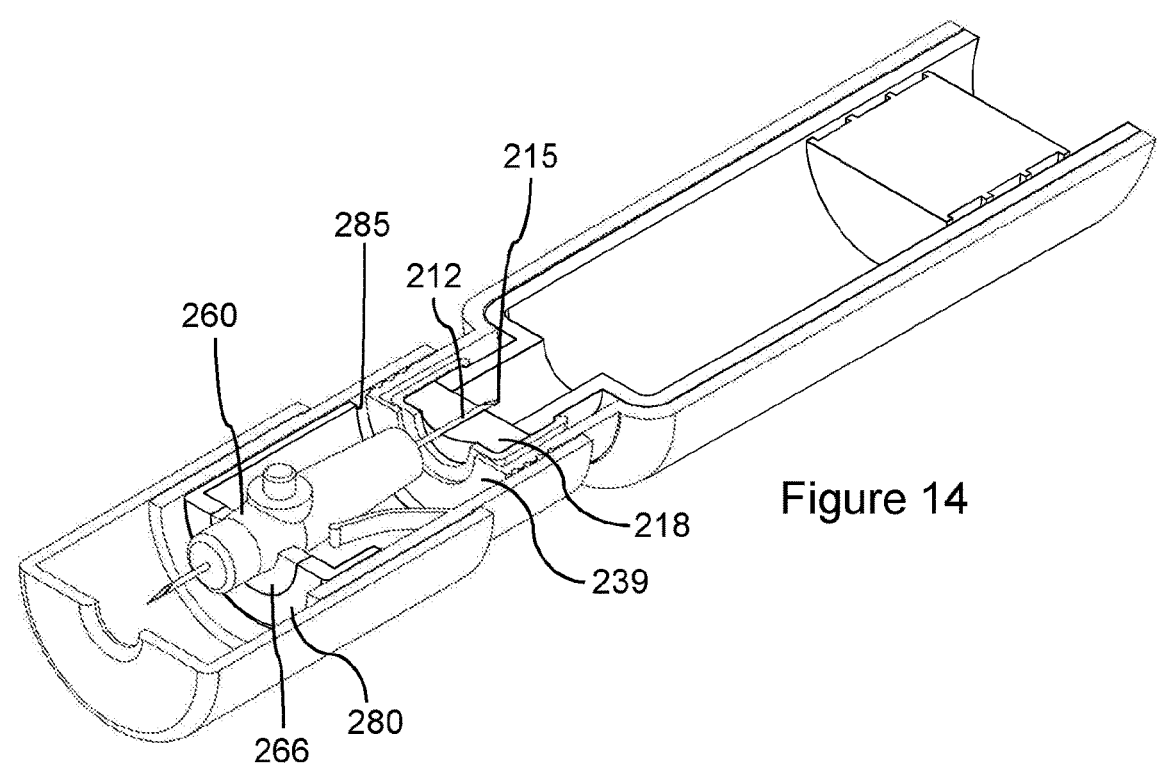
FIG. 14 is a cutaway view of the third preferred embodiment of the safety needle assembly partially attached to a medical injector.

A third preferred embodiment is shown in FIG. 13 to FIG. 17. In this embodiment, the blocking means comprises a control member 280 provided by an annular component 282 coupled with a skirt portion 284. The safety needle assembly 210 is provided with a shielding sleeve 230 which provides shielding to the patient end 214 of the cannula 212 prior to use. In this embodiment as shown in FIG. 14, as the safety needle assembly 210 is screwed onto the injector 211, a lower face 285 of the skirt 284 of the control member 280 abuts an end face 239 of the boss 240 of the injector 211 which thereby forces and moves the control member 280 distally or forwardly with respect to the injector and relative to the tubular housing 220. This movement automatically disengages the control member 280 from the needle mount 260. In particular, the needle mount 260 is provided with a collar 266 to aid this disengagement. The collar 266 provides a step surface which abruptly changes the configuration of the control member 280 from the engaged position to the disengaged position and reliably enables the pivoting movement of the needle mount 260. The skirt 284 of the control member 280 is provided with a cutaway portion in order to accommodate the location of the leaf spring 270 (resilient finger 272) on the internal wall 226 of the tubular housing 220.

As described above, the injection is conducted through urging the front face 231 of the shielding sleeve 230 against the patient's skin to cause the patient end 214 of the cannula 212 to project through the aperture 232 and into the patient to the required depth. On completion of the injection, the shielding sleeve 230 is automatically urged to return to the shielding position by a spring mechanism (not shown).

Figures 15, 16, 17:
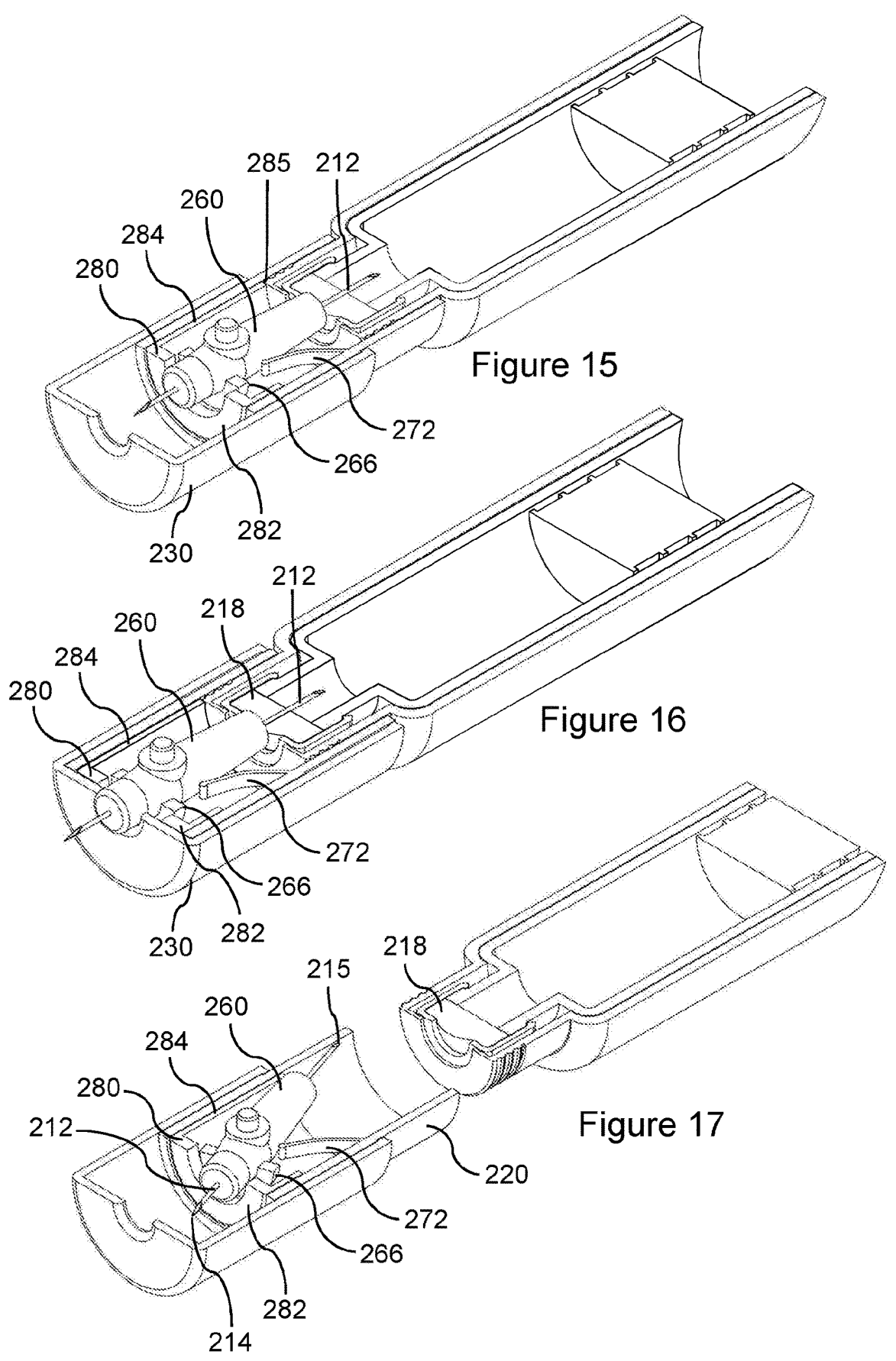
FIG. 15 is a cutaway view of the third preferred embodiment of the safety needle assembly and fully attached to a medical injector.
FIG. 16 is a cutaway view of the third preferred embodiment of the safety needle assembly and a medical injector performing an injection.
FIG. 17 is a cutaway view of the third preferred embodiment of the safety needle assembly after use and disconnected (detached) from a medical injector.
Figures 18, 19:
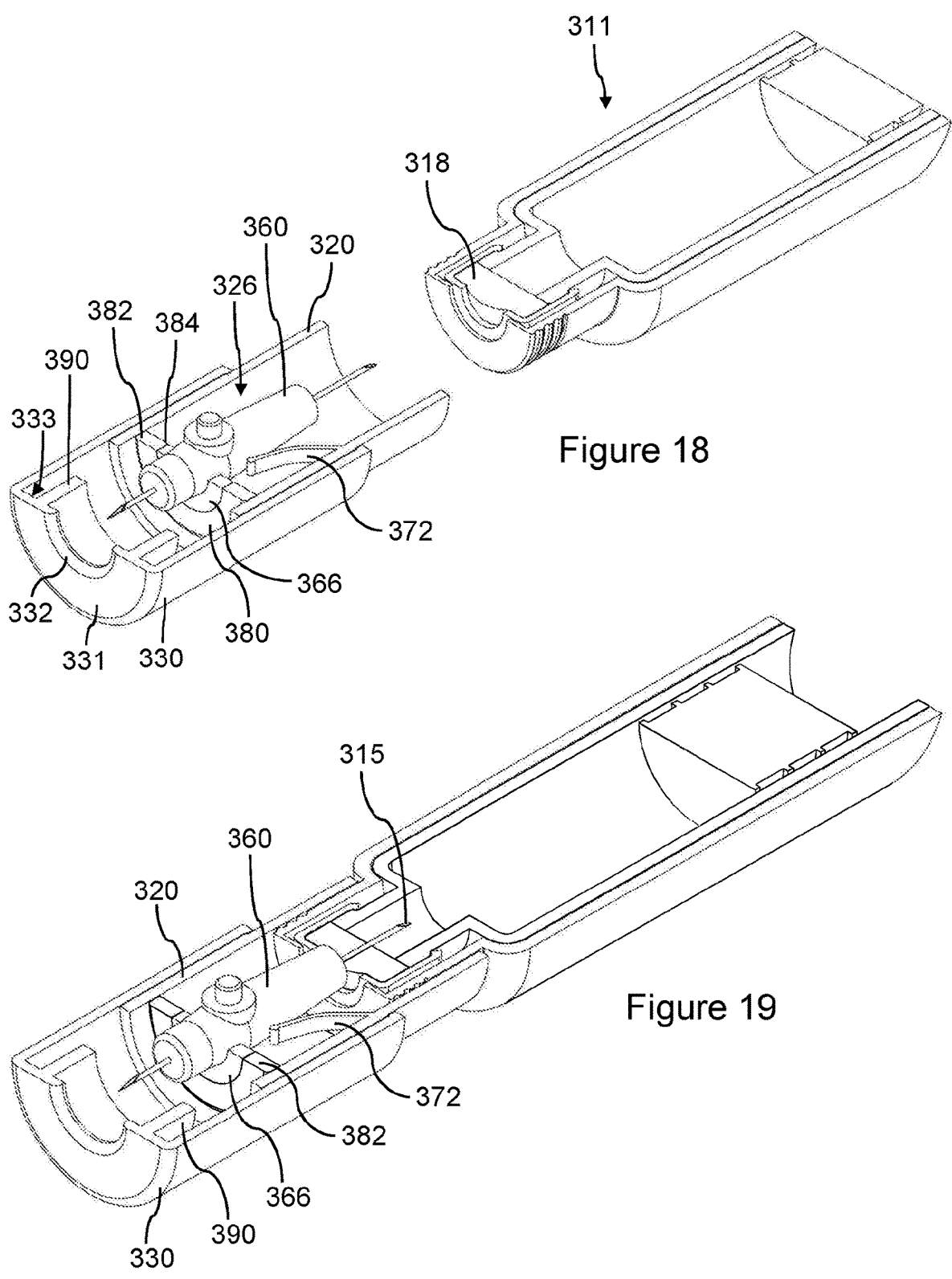
FIG. 18 is a cutaway view of a fourth preferred embodiment of a safety needle assembly prior to attachment to a medical injector.
FIG. 19 is a cutaway view of the fourth preferred embodiment of the safety needle assembly and attached to a medical injector.
Figures 20, 21:
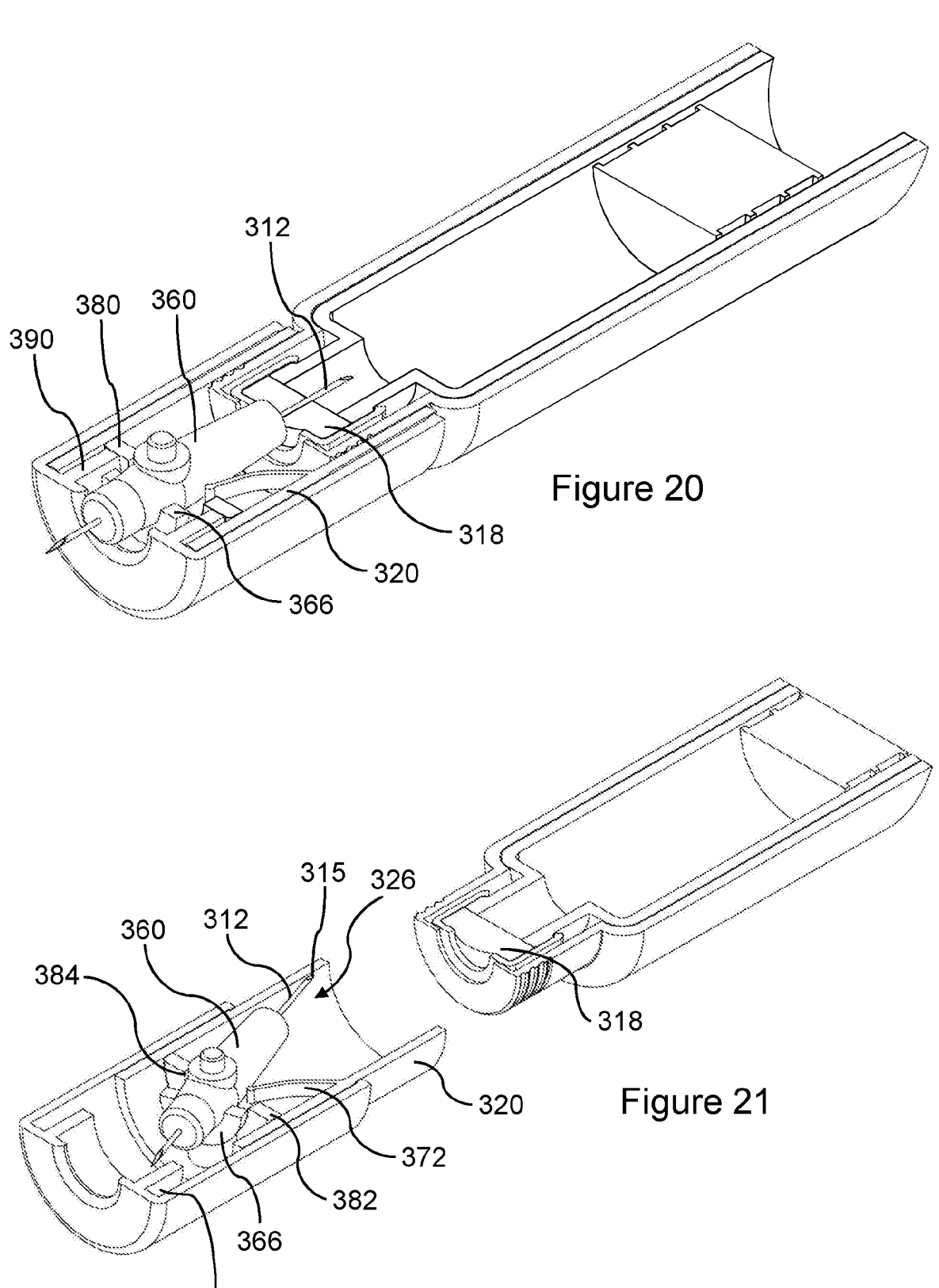
FIG. 20 is a cutaway view of the fourth preferred embodiment of the safety needle assembly and a medical injector performing an injection.
FIG. 21 is a cutaway view of the fourth preferred embodiment of the safety needle assembly after use and disconnected (detached) from a medical injector.

The safety needle assembly 210 is detached from the injector 211 through use of the screw threads 236, 237. The needle mount 260 is now only being held in the operative position through the engagement of the non-patient end 215 of the cannula 212 with the rubber seal 218 such that when removed from the rubber seal 218 the needle mount 260 automatically rotates about the fixed axis 52 to the shielding position. Again, the position of the axis is defined to withdraw the non-patient end 215 of the cannula 212 in a distal direction and continues further into the tubular housing 220 and also cause the non-patient end 215 of the cannula 212 to locate adjacent to the internal wall 226 of the tubular housing 220, as shown in FIG. 17. This preferred embodiment again provides passive needle stick protection to the non-patient end of the needle because the control member 280 is released from the needle mount 260 automatically through securement of the needle safety assembly 210 to the injector 211. In this arrangement, safety needle assembly 210 cannot be attached to an injector 211 and then removed and then attached to the same or another safety needle assembly 210 since the cannula 212 will have been moved to an oblique position which prevents the insertion of the non-patient end 215 through the rubber seal 218 of a medical injector 211. This prevention mechanism applies even if an injection is not performed with the first attachment. As soon as the safety needle assembly 210 is attached to a medical injector 211 it will no longer be possible to attach the same safety needle assembly 210 again.

A fourth preferred embodiment of the present invention is shown in FIG. 18 to FIG. 21. In this embodiment, the blocking means in the form of a control member 380 is provided by an annular component 382 located within the tubular housing 320. In this embodiment, a release means in provided in the form of a disengagement member 390 located on the internal front face 333 of the shielding sleeve 330 and specifically on the internal face of the front face 331 of the shielding sleeve 330. The disengagement member 390 locates around the aperture on the front face 331 of the shielding sleeve 330. This disengagement member 390 in the form of a projection is arranged to move the control member 380 rearwardly or proximally towards the injector 311 as the drug delivery device 308 is used. In some embodiments, the disengagement member 390 may comprise an annular surface or an incomplete annular surface to contact the control member although the disengagement member 390 may comprise one or more projections extending proximally/rearwardly from the internal front face 331 of the shielding sleeve 330. For example, one or more fingers may be used to disengage the control member 380. In particular, as the shielding sleeve 330 is pushed back by the patient's skin towards the injector 311, the disengagement member 390 is also pushed proximally or rearwardly and abuts and moves the control member 380 proximally or rearwardly. This movement of the control member 380 disengages the needle mount 360 from the aperture 384. Again, the control member 380 is an annular component 382 located within the tubular housing 320 and the needle mount 360 comprises a collar 366 to provide a clear step between engagement and disengagement.

In the non-injecting position, the control member 380 is held by one or more detents or is frictionally engaged within the tubular housing 320 to prevent any subsequent engagement of the needle mount 360 by frictional engagement or any other retaining means. As described above, after use, the non-patient end 315 of the cannula 312 is released from the rubber seal 318, there is no means to prevent rotation of the needle mount 360 about the fixed axis. Accordingly, the non-patient end 315 of the cannula is withdrawn longitudinally further into the tubular housing 320 and also moved to the side peripheral wall 326 of the tubular housing 320.

Figures 22, 23:
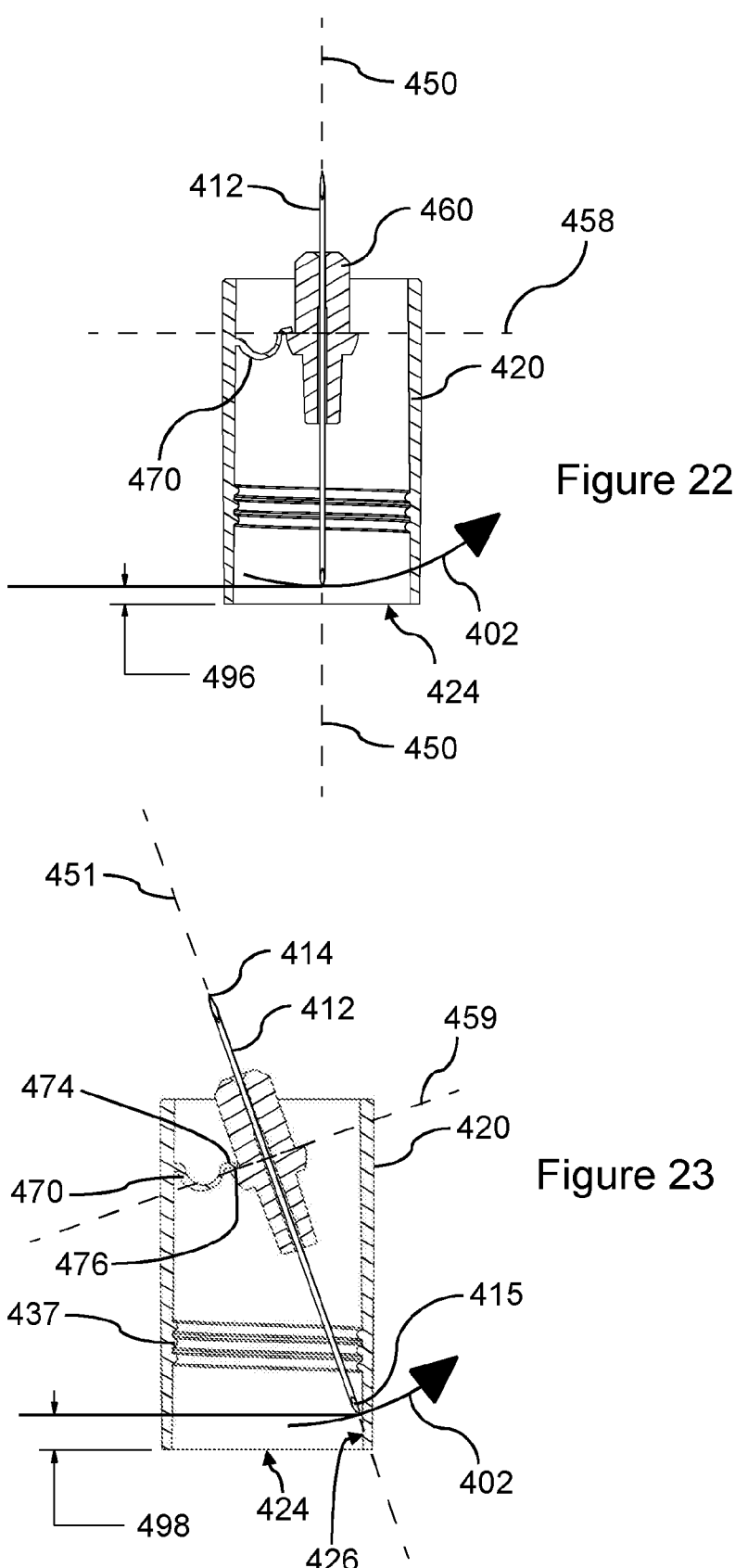
FIG. 22 is a cross section of a tubular housing, a needle and a needle mount of a fifth embodiment of a safety needle assembly with the needle in the operative position.
FIG. 23 is a cross section of the tubular housing, the needle and the needle mount of the fifth embodiment of the safety needle assembly with the needle in the shielding position.

A fifth preferred embodiment comprises a tubular housing 420 together with the needle mount 460 and cannula 412 is shown in FIG. 22 and FIG. 23. These figures schematically show the movement of the non-patient end 415 of the cannula 412 including the simultaneous withdrawal of the non-patient end 415 of the cannula 412 into the tubular housing 420 and movement to the internal wall 426 for shielding purposes. It should be noted that the front (patient) length of the cannula is significantly shorter than the rear (non-patient) length such that the non-patient end 415 of the cannula 412 will rotate to a full extent to abut the internal wall 426 of the tubular housing 420. In particular, the non-patient end 415 of the cannula 412 may abut or locate adjacent to the internal wall 426. A needle having a significantly longer front portion of the needle may not be provided with as good protection since it would be the patient end of the needle which may abut any shielding sleeve which would leave the non-patient end in a more exposed position. In addition, the present invention may provide an axis of rotation for the needle mount intersecting a longitudinal axis and this may seek to maximise the effective withdrawal distance of the non-patient end into the tubular housing and this is optimised by the present invention.

In the operative position, shown on FIG. 22, the needle extends along the central longitudinal axis 450 of the tubular housing. In the shielding position, the cannula 412 extends along an axis 451 which is oblique (see FIG. 23) to the central longitudinal axis 450. During this movement, the perpendicular plane of the needle mount 460/cannula 412 moves/tilts from a first position 458 to a second position 459. The greater the angle between these two positions the greater the potential retraction distance 498 of the non-patient end 415 of the cannula 412 in the shielding position. In this embodiment, the leaf spring 470 will move the needle mount 460 in an anti-clockwise direction 402 with reference to FIG. 22 and FIG. 23.

The separation distance 496 between the non-patient end 415 of the cannula 412 and the proximal open face 424 of the tubular housing 420 may initially be 1 mm in the unused and operative positon, as shown in FIG. 22. In the shielding position optimised position created by the fixed axis of the present invention, this separation distance is increased and, in particular, the final separation distance 498 may be approximately 1.8 mm, as shown in FIG. 23. For example, the present invention may increase the separation distance by 80%. Accordingly, it can be seen that this retraction/withdrawal distance is significantly increased through the use of the fixed axis 52 along the longitudinal axis of the tubular housing.

In this fifth embodiment, it can be seen that the spring means comprises a resilient member or leaf spring including a part of which contacts/engages with and urges down on a flange 476 on a distal part of the flange 476 provided on the needle mount 460. This again creates the torque or moment on the needle mount 460 and a blocking means in the form of a control member is arranged to prevent or allow the needle mount to rotate dependent upon the configuration and state of the drug delivery device.

Figure 24:
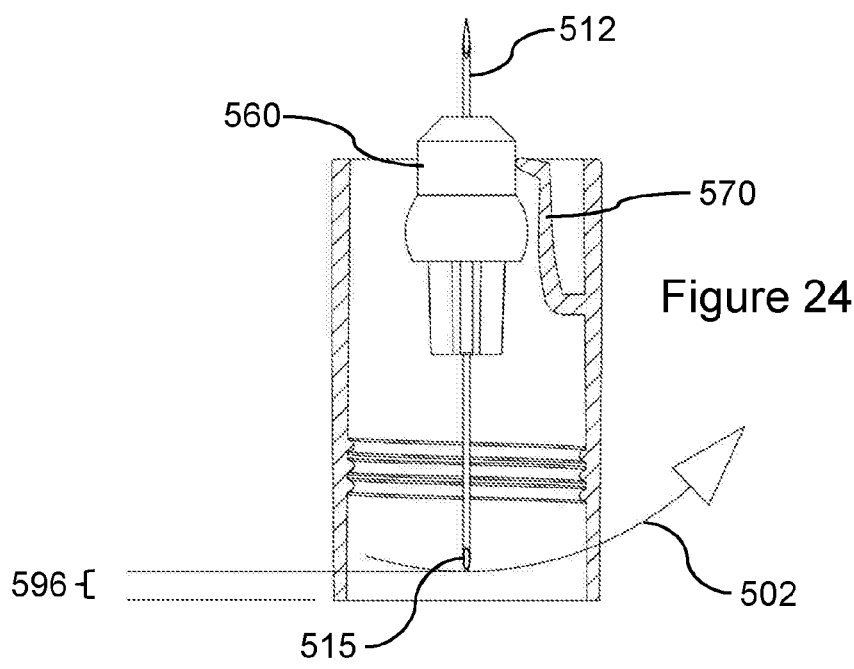
FIG. 24 is a cross section of a tubular housing, a needle and a needle mount of a sixth embodiment of a safety needle assembly with the needle in the operative position.
Figure 25:
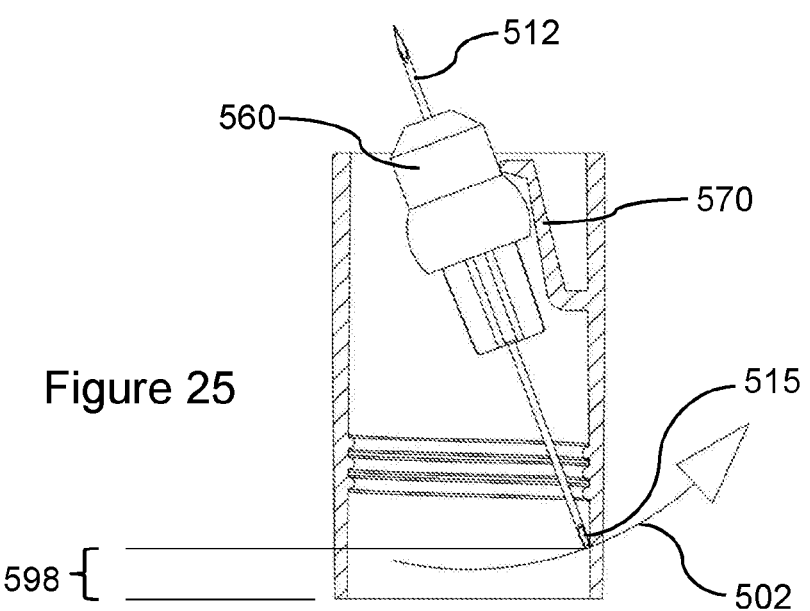
FIG. 25 is a cross section of the tubular housing, the needle and the needle mount of the sixth embodiment of a safety needle assembly with the needle in the shielding position.

In a sixth embodiment of the present invention, the integral leaf spring 570 acts and contacts a forward/distal portion of the needle mount 560, as shown in FIG. 24 and FIG. 25. In this embodiment, the non-patient end 515 of the cannula 512 is again moved to a shielding positon. However, in comparison to the fifth embodiment, in the shielding position, the non-patient end 515 of the cannula 512 locates along the same side of the tubular housing as the leaf spring 570. It will be appreciated that if the leaf spring 570 contacts the needle mount 560 at a position distal/forward of the axis then the leaf spring 570 will move the needle mount 560 in an anti-clockwise direction 502 with reference to FIG. 24 and FIG. 25. Conversely, if the leaf spring 570 did contact the needle mount 560 at a position proximal/rearwardly relative to the axis of rotation then the needle mount 560 is urged in an anti-clockwise direction. In this embodiment, the non-patient end 515 of the cannula 512 travels around the circumferential/arcuate path 502 and the separation distance increases from a first distance 596 to a second distance 598.

Figures 26, 27, 28:
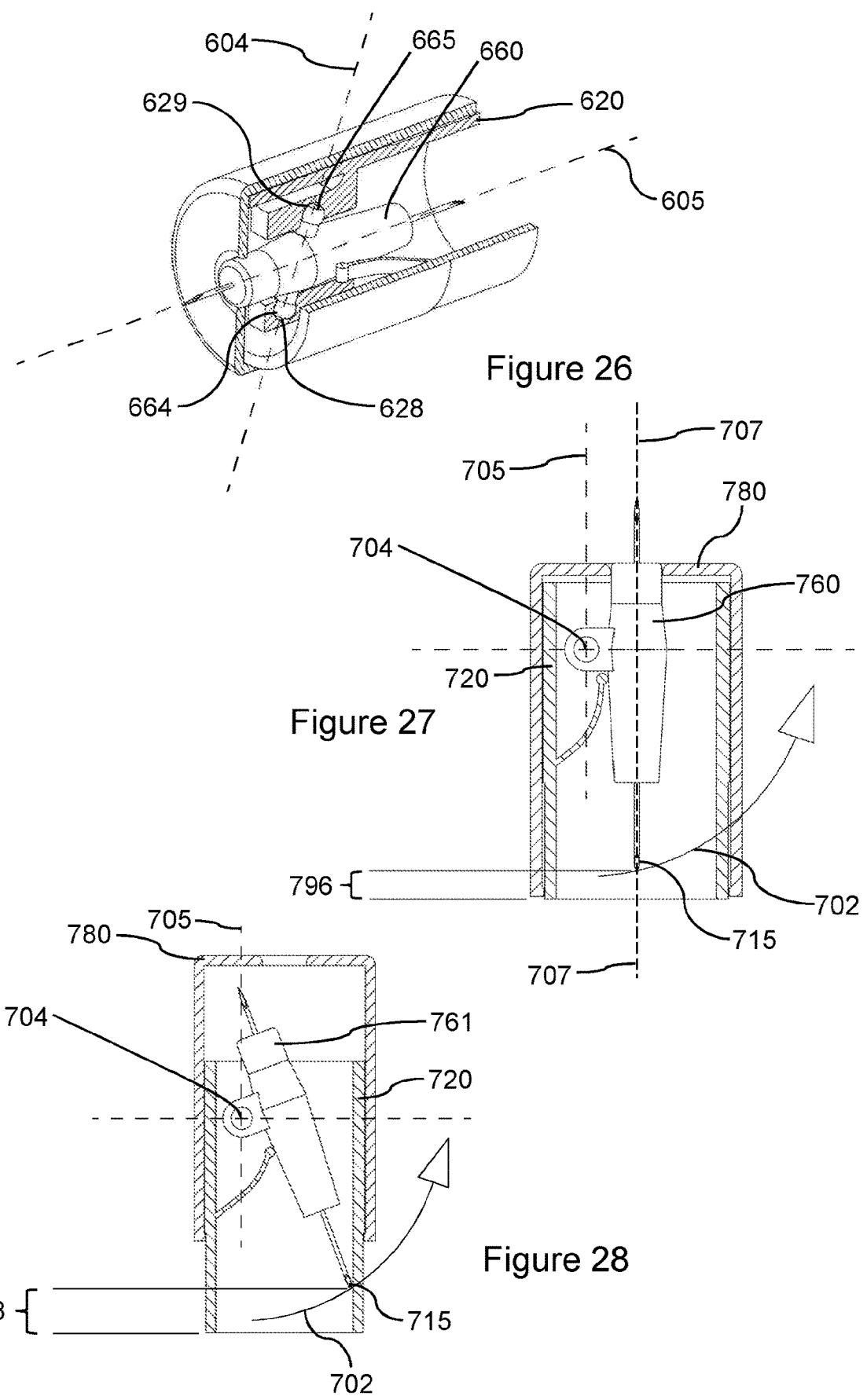
FIG. 26 is a cut away view of a tubular housing, a needle mount, a needle and a shielding sleeve of a seventh embodiment of a safety needle assembly.
FIG. 27 is a cross section of a tubular housing, a needle, a needle mount and a shielding sleeve of an eighth embodiment of a safety needle assembly with the needle in the operative position.
FIG. 28 is a cross section of the tubular housing, the needle, the needle mount and the shielding sleeve of the eighth embodiment of a safety needle assembly with the needle in the shielding position.

As shown in FIG. 26, a seventh embodiment includes an axis of rotation 604 of the needle mount 660 which is at an oblique angle (and not radial) with respect to the longitudinal axis 605 of the tubular housing 620. In particular, the axis of rotation 604 is at an oblique angle relative to a radius or diameter of the tubular housing 620. As it can be seen, the tubular housing 620 provides two offset recesses 628, 629. Similarly, the needle mount 660 has two corresponding offset lugs 664, 665. This arrangement of corresponding lugs 664, 665 and recesses 628, 629 provides ball and socket joints to aid the pivoting motion of the needle mount 660.

Finally, an eighth embodiment of the present invention is shown in FIG. 27 and FIG. 28 which shows that the needle mount 760 is arranged to rotate about an axis 704 which is located offset from the central longitudinal axis 707 of the tubular housing 720. An outer surface 761 of the front portion of the needle mount 760 may again be arranged to be engaged by the control member 780. The axis of rotation 704 still locates along a longitudinal axis 705 of the tubular member but this longitudinal axis not is not the central longitudinal axis of the tubular housing 720. In this embodiment, it can be seen that the offset location of the axis or rotation 704 can increase the retraction distance 796, 798 for the non-patient end 715 of the cannula 712 on moving to the shielding position. This results from the increase in the length of the arcuate travel path 702 of the non-patient end 715 and this thereby increases the final separation distance 798.

In summary, the present invention comprises a needle mount comprising a unitary component with integral axle mounts and the tubular housing also comprises a unitary component with an integral leaf spring and axle mounts. These unitary components reduce complexity and cost and simplify assembly during manufacture.

The needle/cannula is fixedly retained in a position so as to pivot around an axis radial to the central axis of the housing. This prevents and stops proximal rearward movement of the needle mount as may occur In the present invention, spring means urges rotation of the cannula about an axis so as to move the non-patient end of the cannula distally/forwardly. Such forwards/distal movement is advantageous and reduces the chance of needle stick injuries.

A control member is located within and/or adjacent to an end of the tubular housing and is slidably displaceable along the central axis of the housing. As is shown a number of the embodiments described above, such longitudinal movement is automatic and is significantly more reliable than alternative movements within such intricate designs and a radial movement to disengage from the needle mount may be unreliable and create difficulties in assembly and manufacture.

The present invention may be incorporated and used with existing devices providing front end protection against needle stick injuries, for example as shown in WO2011/092518.

Overall, as described above, each embodiment comprises a movable control member to engage with a needle mount. In a set position, the needle mount is held in an operative position by the control member even though an urging torque or moment is exerted on the needle mount by a spring means. Thereafter attachment of the safety needle assembly to the medical injector, the use thereof and subsequent detachment of the safety needle assembly from the medical injector, causes the control member to move away from the set position. The control member thereby allows the spring means to rotate the needle to the shielding position and to move the non-patient end of the needle towards the distal end of the tubular housing. In this shielding position the needle extends at an angle oblique to the central longitudinal axis of the tubular housing to place the non-patient end of the needle at a location adjacent to an interior wall of the tubular housing. The non-patient end moves along a circumferential path such that the non-patient end is retracted into or withdrawn further into the tubular housing.

An existing prior art device relating to the prevention of back needle stick injuries is shown in WO2010/079016. This device includes a radially moving release part which disengages a part within which a needle is mounted. This device includes a spring which is arranged to move the shield forwardly/distally. This spring acts on the cannula to tilt the cannula and moves the cannula against a skirt. However, the spring does not retract the non-patient end of the cannula and the arrangement tends to urge the non-patient end proximally/rearwardly towards the open end of the skirt.

The present invention protects the non-patient end of a pen needle located within a tubular housing. A spring is arranged to urge rotation of the needle about an axis which either intersects a longitudinal axis of the needle or a longitudinal axis of the tubular housing which may be offset from the longitudinal axis of the needle. The spring urges and causes the needle mount to move in a direction which would retract the non-patient end of the cannula. In some embodiments the axis of rotation may be generally perpendicular to a longitudinal axis of the needle and in other embodiments the axis of rotation may be oblique to a longitudinal axis of the needle. However, a control member prevents rotation of the needle mount. As the pen needle is screwed onto to the pen injector, the non-patient end of the needle pierces the rubber seal of the cartridge and enters into the drug reservoir within the pen injector. The needle is inserted into the patient and the drug is then injected. The pen needle is subsequently removed from injection site. However, the needle mount cannot rotate (even though the control member is no longer preventing rotation of the needle mount) because the non-patient end of the needle in inserted in the rubber seal of the pen injector drug reservoir. When the pen injector is disconnected (detached) the spring can then rotate the needle mount to "safely park" the non-patient end of the needle to help prevent accidental needle stick injuries.

The invention claimed is:

1. A safety needle assembly for use with a medical injector comprising;
   a tubular housing removably attachable to the medical injector, the tubular housing extending in a longitudinal direction from a proximal end to a distal end, the proximal end being arranged for attachment to the medical injector;

a needle mount located within the tubular housing for directly or indirectly supporting a double ended needle having a patient end and a non-patient end, the needle mount being arranged to allow movement of the needle, including rotation about an axis of rotation, from an operative position to a shielding position;
   a spring member to urge movement of the needle to the shielding position; and
   a releasable blocking member arranged to prevent movement of the needle from the operative position whereat the needle extends in a direction along a longitudinal axis of the tubular housing and whereby release of the blocking member allows movement of the needle to the shielding position;
   wherein the needle mount is a unitary component inserted into the tubular housing and fixedly retained in the tubular housing to fix the axis of rotation of the needle relative to the tubular housing, the axis of rotation intersecting the longitudinal axis of the tubular housing, and the spring member arranged to urge rotation of the needle about said axis of rotation; and
   wherein the blocking member comprises a control member slidably displaceable along the longitudinal axis of the tubular housing from a set position whereat the control member engages the needle mount to maintain the needle in the operative position before use, and thereafter, attachment of the safety needle assembly to the medical injector, the use thereof, and subsequent detachment of the safety needle assembly from the medical injector, causes the control member to move away from the set position and disengage from the needle mount to allow the spring member to move the non-patient end of the needle towards the distal end of the tubular housing by rotating the needle to the shielding position whereat the needle extends at an angle oblique to the longitudinal axis of the tubular housing to place the non-patient end of the needle at a location adjacent to an interior wall of the tubular housing.

2. The safety needle assembly according to claim 1, in which the attachment of the safety needle assembly to the medical injector, the use thereof, and subsequent detachment of the safety needle assembly from the medical injector, causes the control member to move away from the set position and disengage from the needle mount to allow the spring member to rotate the needle to the shielding position, wherein the spring member is arranged to ensure that the non-patient end of the needle moves distally and not proximally.

3. The safety needle assembly according to claim 1, in which the position of the axis of rotation is defined to: withdraw the non-patient end of the needle in the distal direction and further into the tubular housing, and cause the non-patient end of the needle to locate adjacent to the interior wall of the tubular housing.

4. The safety needle assembly according to claim 1, wherein the axis of rotation is statically fixed relative to the tubular housing and the non-patient end moves in a circumferential path about the axis of rotation from the operative position to the shielding position.

5. The safety needle assembly according to claim 1, in which, in the shielding position, the non-patient end of the needle contacts the interior wall, which is an internal peripheral wall of the tubular housing.

6. The safety needle assembly according to claim 1, wherein the control member comprises an engagement aperture and a part of the needle mount is arranged, in the set position, to locate within the engagement aperture to prevent rotation of the needle from the operative position.

7. The safety needle assembly according to claim 6, in which the control member comprises an annular member and the engagement aperture is located centrally on the annular member.

8. The safety needle assembly according to claim 6, in which the needle mount comprises a collar which locates within the aperture of the control member in the set position.

9. The safety needle assembly according to claim 1, in which the spring member comprises a resilient member which extends inwardly from the tubular housing and contacts an outer surface of the needle mount at a position offset from the axis of rotation.

10. The safety needle assembly according to claim 1, in which the spring member comprises a leaf spring projecting inwardly from the tubular housing and, with the needle in an operative position, the leaf spring is in a deflected position relative to a neutral position.

11. The safety needle assembly according to claim 10, in which an end surface of the leaf spring contacts an outer longitudinal surface of the needle mount to create a torque about the axis of rotation.

12. The safety needle assembly according to claim 1, in which the needle mount comprises a unitary component having axial members located on an outer surface.

13. The safety needle assembly according to claim 12, in which the tubular housing comprises axial members located on an internal surface for cooperation with the axial members provided on the needle mount.

14. The safety needle assembly according to claim 13, in which the axial members of the needle mount and the axial members of the tubular housing enable a push fit engagement of the needle mount into the tubular housing to fixedly retain the needle mount in the tubular housing.

15. The safety needle assembly according to claim 13, wherein the axial members of the tubular housing and the axial members of the needle mount comprise a first pair of axial members comprising projecting portions and a second pair of axial members comprising corresponding recesses.

16. The safety needle assembly according to claim 15, in which the projecting portions comprise hemi-spherical projections.

17. The safety needle assembly according to claim 1, in which the control member is mounted to move away from the proximal end of the tubular housing in order to disengage the needle mount.

18. The safety needle assembly according to claim 1, comprising a needle shielding sleeve and, in which, the control member comprises a distal end face of the needle shielding sleeve which provides an engagement aperture to prevent rotation of the needle from the operative position whilst the control member is in the set position.

19. The safety needle assembly according to claim 1, in which the control member comprises a disc, the disc being located within a needle shielding sleeve of the safety needle assembly and wherein the disc is slidably displaceable in the needle shielding sleeve from the set position, and wherein the control member is frictionally engaged in the needle shielding sleeve and is maintained in a position located adjacent to a distal end of the needle shielding sleeve on movement thereto by the tubular housing during an injection.

20. The safety needle assembly according to claim 1, in which the control member comprises a distal end face and a skirt portion extending therefrom, the distal end face comprising an aperture for engaging an outer surface of the needle mount in the set position and the skirt providing a contact face which is contacted by part of the medical injector in the set position, and the control member is moved from the set position on attachment of the safety needle assembly to the medical injector.

21. The safety needle assembly according to claim 1, in which the control member is mounted to move towards the proximal end of the tubular housing in order to disengage the needle mount.

22. The safety needle assembly according to claim 21, in which a needle shielding sleeve encompasses and shields the patient end of the needle in a non-injecting configuration and, in which, the needle shielding sleeve comprises a release member to slidably displace the control member from the set position.

23. A drug delivery device comprising a safety needle assembly and a medical injector, the safety needle assembly being in accordance with claim 1.

24. The drug delivery device according to claim 23, in which the medical injector comprises a rubber seal and attachment of the safety needle assembly to the medical injector causes the non-patient end of the needle to pierce and penetrate through the rubber seal and wherein the position of the non-patient end though the rubber seal maintains the needle in the operative position after the control member has moved from the set position.

25. A method of shielding a non-patient end of a needle in a safety needle assembly for use with a medical injector, the safety needle assembly comprising;

a tubular housing removably attachable to the medical injector, the tubular housing extending in a longitudinal direction from a proximal end to a distal end, the proximal end being arranged for attachment to the medical injector;

a needle mount located within the tubular housing for directly or indirectly supporting a double ended needle having a patient end and a non-patient end, the needle mount being arranged to allow movement of the needle, including rotation about an axis of rotation, from an operative position to a shielding position;

a spring member to urge movement of the needle to the shielding position; and a releasable blocking member arranged to prevent movement of the needle from the operative position whereat the needle extends in a direction along a longitudinal axis of the tubular housing and whereby release of the blocking member allows movement of the needle to the shielding position;

wherein the needle mount is a unitary component inserted into the tubular housing and fixedly retained in the tubular housing to fix the axis of rotation of the needle relative to the tubular housing, the axis of rotation intersecting the longitudinal axis of the tubular housing, and the spring member arranged to urge rotation of the needle about said axis of rotation; and wherein the method comprises;

slidably displacing a control member of the blocking member along the longitudinal axis of the tubular housing from a set position whereat the control member engages the needle mount to maintain the needle in an operative position before use by:

attaching the safety needle assembly to the medical injector, performing an injection using the safety needle assembly and the medical injector, and subsequently detaching the safety needle assembly from the medical injector, which causes the control member to move away from the set position and disengage from the needle mount to allow the spring member to move the non-patient end of the needle towards the distal end of the tubular housing by rotating the needle to the shielding position whereat the needle extends at an angle oblique to the longitudinal axis of the tubular housing to place the non-patient end of the needle at a location adjacent to an interior wall of the tubular housing.

\*　\*　\*　\*　\*